(12) United States Patent
Emonds-Alt et al.

(10) Patent No.: US 7,521,449 B2
(45) Date of Patent: Apr. 21, 2009

(54) 4-ARYLMORPHOLIN-3-ONE DERIVATIVES, THEIR PREPARATION AND THERAPEUTIC USE THEREOF

(75) Inventors: Xavier Emonds-Alt, Combaillaux (FR); Vincenzo Proietto, Saint-Georges-d'Orques (FR)

(73) Assignee: Sanofi-Aventis, Paris (FR)

( * ) Notice: Subject to any disclaimer, the term of this patent is extended or adjusted under 35 U.S.C. 154(b) by 267 days.

(21) Appl. No.: 11/621,224

(22) Filed: Jan. 9, 2007

(65) Prior Publication Data

US 2007/0142349 A1    Jun. 21, 2007

Related U.S. Application Data

(63) Continuation of application No. PCT/FR2005/001852, filed on Jul. 20, 2005.

(30) Foreign Application Priority Data

Jul. 23, 2004    (FR) .................................. 04 08222

(51) Int. Cl.
A61K 31/5377 (2006.01)
C07D 413/06 (2006.01)

(52) U.S. Cl. .................... 514/237.2; 544/106; 544/111; 544/129; 544/130; 514/231.2; 514/231.5; 514/235.5

(58) Field of Classification Search ................. 544/106, 544/111, 124, 129, 130; 514/231.2, 231.5, 514/235.5, 237.2
See application file for complete search history.

(56) References Cited

U.S. PATENT DOCUMENTS 5,641,777 A    6/1997    Emonds-Alt et al.

| | | |
|---|---|---|
| 6,028,082 A | 2/2000 | Bichon et al. |
| 6,159,967 A | 12/2000 | Nishi et al. |
| 6,288,059 B1 | 9/2001 | Nishi et al. |
| 6,506,750 B1 * | 1/2003 | Ducoux et al. ........... 514/235.8 |
| 6,951,940 B2 * | 10/2005 | Ducoux et al. .............. 544/360 |

FOREIGN PATENT DOCUMENTS

| WO | WO 98/04561 | 2/1998 |
|---|---|---|
| WO | WO 00/58292 | 10/2000 |
| WO | WO 02/094821 | 11/2002 |

* cited by examiner

*Primary Examiner*—Golam M Shameem
(74) *Attorney, Agent, or Firm*—Craig M. Bell

(57) ABSTRACT

The invention relates to compounds corresponding to formula (I):

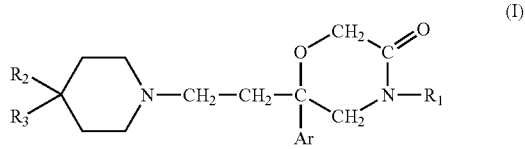

in which:
Ar represents a mono- or disubstituted phenyl;
$R_1$ represents an unsubstituted or substituted phenyl;
$R_2$ represents:
  a pyridyl;
  an unsubstituted or substituted phenyl;
  a benzyl that is unsubstituted or substituted on the phenyl;
$R_2$ may moreover represent:
  a heterocyclic radical;
$R_3$ represents various values.

The invention also comprises methods for the compounds preparation, formulations comprising them and therapeutic applications thereof.

8 Claims, No Drawings

4-ARYLMORPHOLIN-3-ONE DERIVATIVES, THEIR PREPARATION AND THERAPEUTIC USE THEREOF

CROSS-REFERENCE TO RELATED APPLICATIONS

This application is a continuation of International Patent Application No. PCT/FR2005/001852 filed on Jul. 20, 2005 which is incorporated herein by reference in its' entirety which also claims the benefit of priority of French Patent Application No. 0408222 filed on Jul. 23, 2004.

FIELD OF THE INVENTION

The present invention relates generally to compounds for the treatment of diseases of the central nervous system, in particular, inflammation and psychiatric disorders, among others. More specifically, the invention relates to compounds and formulations comprising them for the treatment of diseases such as gastro-intestinal inflammation, neuropathic pain and mental psychoses and depression. The present invention more specifically is directed to compounds that exhibit a high affinity for human neurokinin A receptors $NK_2$ and which are antagonists of the said receptors, i.e., novel 4-arylmorpholin-3-one derivatives, as well as methods for their preparation and therapeutic applications thereof.

BACKGROUND OF THE INVENTION

Neurokinin A (NKA) is part of a group of neuropeptides known as tachykinins or neurokinins, which includes substance P (SP) and neurokinin B (NKB). The biological effects of neurokinin A and of the other tachykinins are mediated by specific receptors of the family of protein-G-coupled transmembrane 7-domain receptors known as $NK_1$, $NK_2$ and $NK_3$. The tachykinin receptor $NK_2$ binds neurokinin A, while the receptors $NK_1$ and $NK_3$ bind, respectively, substance P and neurokinin B see for example, Pennefather J. N. et al., Life Sci., 2004, 74, 1445-1463. The tachykinin receptors $NK_2$ are very widely expressed in the peripheral nervous system where they mediate the wide variety of effects produced by neurokinin A, especially, and in a non-limiting manner, in the respiratory system (bronchoconstriction, coughing, inflammation, bronchial hyperactivity, etc.) (Joos G. F., Hand. Exp. Pharm., 2004, 164, 491-510; Advenier C. et al., Eur. Respir. J., 1997, 10, 1892-1906), the gastrointestinal system (inflammation, infection, motility, pain, etc.) (Holzer P. Hand. Exp. Pharm., 2004, 164, 511-55) and the urinary system (vesical hyperactivity, inflammation, infection, etc.) (Kiss S. et al., Neurosci. Lettrs., 2001, 313, 57-60; Warner F. J. et al., Eur. J. Pharmacol., 2002, 438, 171-177). The tachykinin receptor $NK_2$ is also expressed in the brain (Hagan R. M. et al., Regul. Pept., 1993, 46, 9-19; Steinberg R., et al., Eur. J. Neurosci., 1998, 10, 2337-2345; Bensaid M., et al., Neurosci. Lett., 2001, 303, 25-28; Saffroy M. et al., J. Neurochem., 2001, 79, 985-996; Saffroy M. et al., Neuroscience, 2003, 116, 761-773) and the spinal column (Yashpal K. et al., Brain Res., 1990, 506, 59-266), where it mediates the central effects of neurokinin A.

By way of example, experimental data shows that blocking the tachykinin receptor $NK_2$ with an antagonist may be a treatment for major depression (Emonds-Alt, Handb Exp. Pharm., 2004, 219-244) and also functional and painful gastrointestinal disorders such as irritable bowel syndrome (IBS) (Emonds-Alt, Handb Exp. Pharm., 2004, 219-244; Lecci A. et al., Br. J. Pharmacol., 2004, 141, 1249-1263).

Many prior art patents or patent applications describe compounds that exhibit a proclivity for binding to the tachykinin receptors. For example, international patent application WO 96/23787 discloses compounds of formula A:

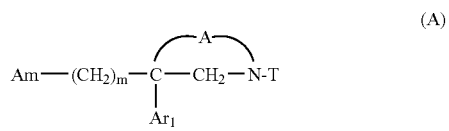

(A)

in which, especially:

A may represent the divalent radical $-O-CH_2-CO-$;

Am, m, $Ar_1$ and T have different values.

The compounds (A) show affinity for the tachykinin receptors $NK_1$, $NK_2$ or $NK_3$ in general.

Patent application EP-A-0 776 893 concerns compounds of formula B:

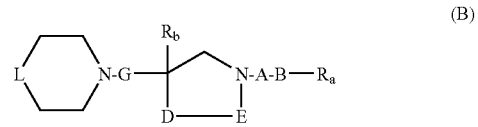

(B)

in which, especially:

D-E may represent a divalent radical $-O-CH_2-CH_2-$;

L, G, E, A, B, $R_a$ and $R_b$ have different values.

The compounds (B) are antagonists of both tachykinin receptors $NK_1$ and $NK_2$.

Patent application WO 00/34274 teaches and claims cyclohexylpiperidine derivatives that are antagonists of both the substance P receptors $NK_1$ and the neurokinin A receptors $NK_2$.

Patent application WO 02/094821 discloses morpholine derivatives that are antagonists of both human tachykinin receptors $NK_2$ and $NK_3$.

The novel compounds of the present invention show a very strong affinity for the human neurokinin A receptors $NK_2$ and are antagonists of said receptors.

Furthermore, the compounds according to the present invention show good bioavailability when they are administered orally and subsequently cross the blood-brain barrier.

SUMMARY OF THE INVENTION

The invention relates to compounds corresponding to formula (I):

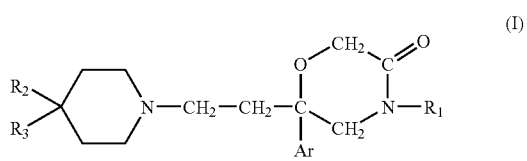

(I)

in which:

Ar represents a mono- or disubstituted phenyl;

$R_1$ represents an unsubstituted or substituted phenyl;

$R_2$ represents:
- a pyridyl;
- an unsubstituted or substituted phenyl;
- a benzyl that is unsubstituted or substituted on the phenyl;

$R_2$ may moreover represent:
- a heterocyclic radical;

$R_3$ represents various values.

The invention also comprises methods for the compounds preparation, formulations comprising them and therapeutic applications thereof.

DETAILED DESCRIPTION OF THE INVENTION

One subject of the present invention are compounds corresponding to formula (I):

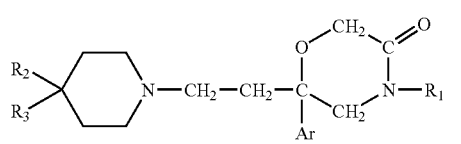
(I)

in which:
- Ar represents a phenyl mono- or di-substituted with a halogen atom;
- $R_1$ represents a phenyl that is unsubstituted or substituted once or twice with one or two substituents independently chosen from a halogen atom, a $(C_1-C_4)$alkyl and a $(C_1-C_4)$alkoxy;
- $R_2$ represents:
  - a pyridyl;
  - a phenyl that is unsubstituted or substituted once or twice with one or two substituents independently chosen from a halogen atom, a $(C_1-C_4)$alkyl, a $(C_1-C_4)$alkoxy, a tri-fluoromethyl group and a tri-fluoromethoxy group;
  - a benzyl that is unsubstituted or substituted on the phenyl once or twice with one or two substituents independently chosen from a halogen atom, a $(C_1-C_4)$alkyl, a $(C_1-C_4)$alkoxy, a tri-fluoromethyl group and a tri-fluoromethoxy group;
- $R_2$ may also represent:
  - a heterocyclic radical chosen from azetidine, pyrrolidine, piperidine, morpholine, thiomorpholine and perhydroazepine when $R_3$ represents a cyano or a group $—CONR_{11}R_{12}$;
- $R_3$ represents a group chosen from:
  - (1) a hydrogen atom;
  - (2) $(C_1-C_4)$alkyl;
  - (3) $(C_1-C_4)$alkylcarbonyl;
  - (4) cyano;
  - (5) $—(CH_2)_q—OH$;
  - (6) $—(CH_2)_q—O—(C_1-C_4)$alkyl;
  - (7) $—(CH_2)_q—O—CO—R_4$;
  - (8) $—(CH_2)_q—O—CO—NH—(C_1-C_4)$alkyl;
  - (9) $—NR_5R_6$;
  - (10) $—(CH_2)_q—NR_7COR_8$;
  - (11) $—(CH_2)_q—NR_7COOR_9$;
  - (12) $—(CH_2)_q—NR_7SO_2R_{10}$;
  - (13) $—(CH_2)_q—NR_7CONR_{11}R_{12}$;
  - (14) $—CH_2NR_{13}R_{14}$;
  - (15) $—CH_2—CH_2NR_{13}R_{14}$;
  - (16) $—COOH$;
  - (17) $—COO—(C_1-C_4)$alkyl;
  - (18) $—CONR_{11}R_{12}$;
  - (19) $—CH_2—COOH$;
  - (20) $—CH_2—COO—(C_1-C_4)$alkyl;
  - (21) $—CH_2—CONR_{11}R_{12}$;
  - (22) $—O—CH_2CH_2OR_{15}$;
  - (23) $—NR_7COCOR_{16}$;
  - (24) $—CONR_7—NR_{17}R_{18}$;

(25) 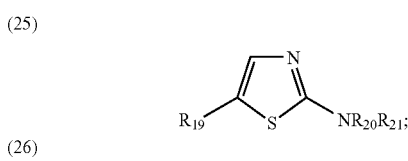

(26) 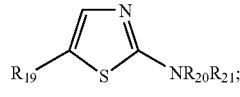

q is 0, 1 or 2;
$R_4$ represents a $(C_1-C_4)$alkyl; a $(C_3-C_7)$cycloalkyl that is unsubstituted or substituted with one or more methyls; a phenyl; a pyridyl;
$R_5$ and $R_6$ each independently represent a hydrogen atom or a $(C_1-C_4)$alkyl; $R_6$ may also represent a $(C_3-C_7)$cycloalkylmethyl, a benzyl or a phenyl; or $R_5$ and $R_6$, together with the nitrogen atom to which they are attached, constitute a heterocycle chosen from azetidine, pyrrolidine, piperidine, morpholine thiomorpholine, perhydroazepine or piperazine that is unsubstituted or substituted in position 4 with a $(C_1-C_4)$ alkyl;
$R_7$ represents a hydrogen atom or a $(C_1-C_4)$alkyl;
$R_8$ represents a hydrogen atom; a $(C_1-C_4)$alkyl; a vinyl; a phenyl; a benzyl; a pyridyl; a $(C_3-C_7)$cycloalkyl that is unsubstituted or substituted with one or more methyl groups; a furyl; a thienyl; a pyrrolyl; an imidazolyl;
or $R_7$ and $R_8$ together represent a group $—(CH_2)_p—$ wherein p is 3 or 4;
$R_9$ represents a $(C_1-C_4)$alkyl or a phenyl;
or $R_7$ and $R_9$ together represent a group $—(CH_2)_n—$ wherein n is 2 or 3;
$R_{10}$ represents a $(C_1-C_4)$alkyl; an amino that is free or substituted with one or two $(C_1-C_4)$alkyls; a phenyl that is unsubstituted or substituted one or more times with a substituent chosen from: a halogen atom, a $(C_1-C_4)$alkyl, a trifluoromethyl, a hydroxyl, a $(C_1-C_4)$alkoxy, a carboxyl, a $(C_1-C_4)$alkoxycarbonyl, a $(C_1-C_4)$alkylcarbonyloxy, a cyano, a nitro, an amino that is free or substituted with one or two $(C_1-C_4)$alkyls, the said substituents being identical or different;
$R_{11}$ and $R_{12}$ each independently represent a hydrogen or a $(C_1-C_4)$alkyl; $R_{12}$ may also represent a $(C_3-C_7)$cycloalkyl, $(C_3-C_7)$cycloalkylmethyl, a hydroxyl, a $(C_1-C_4)$alkoxy, a benzyl or a phenyl; or $R_{11}$ and $R_{12}$, together with the nitrogen atom to which they are attached, constitute a heterocycle chosen from azetidine, pyrrolidine, piperidine, morpholine thiomorpholine and perhydroazepine;
or $R_7$ and $R_{12}$ together represent a group $—(CH_2)_m—$ wherein m is 2 or 3;
$R_{13}$ and $R_{14}$ each independently represent a hydrogen atom or a $(C_1-C_4)$alkyl; $R_{14}$ may also represent a $(C_3-C_7)$cycloalkylmethyl or a benzyl;

$R_{15}$ represents a hydrogen atom; a $(C_1-C_4)$alkyl; a formyl; a $(C_1-C_4)$alkylcarbonyl;

$R_{16}$ represents a $(C_1-C_4)$alkoxy;

$R_{17}$ and $R_{18}$ each independently represent a hydrogen atom or a $(C_1-C_4)$alkyl;

or alternatively $R_{17}$ and $R_{18}$, together with the nitrogen atom to which they are attached, constitute a heterocycle chosen from pyrrolidine, piperidine and morpholine;

$R_{19}$ represents a hydrogen atom or a $(C_1-C_4)$alkyl;

$R_{20}$ and $R_{21}$ each independently represent a hydrogen atom or a $(C_1-C_4)$alkyl; $R_{21}$ may also represent a formyl or a $(C_1-C_4)$alkylcarbonyl.

The compounds of formula (I) may also comprise one or more asymmetric carbon atoms. They may thus exist in the form of their enantiomers or diastereoisomers. These enantiomers and diastereoisomers, and also mixtures thereof, including racemic mixtures, comprise an aspect of the invention.

The compounds of formula (I) may also exist in the form of their bases or as their acid-addition salts. Such addition salts comprise a part of the invention.

These salts are advantageously prepared with pharmaceutically acceptable acids, but the salts of other acids that are useful for purifying or isolating the compounds of formula (I) also comprise a part of the invention.

The compounds of formula (I) may also exist in the form of their hydrates or solvates, i.e. in the form of associations or combinations with one or more water molecules or with a solvent. Such hydrates and solvates also form part of the invention.

The term "halogen atom" means a bromine, chlorine, fluorine or iodine atom.

The term "$(C_1-C_4)$alkyl" means a linear or branched alkyl radical of one to four carbon atoms, such as a methyl, ethyl, propyl, isopropyl, butyl, isobutyl, sec-butyl or tert-butyl radical.

The term "$(C_1-C_4)$alkoxy" means a linear or branched alkoxy radical of one to four carbon atoms, such as a methoxy, ethoxy, propoxy, isopropoxy, butoxy, isobutoxy, sec-butoxy or tert-butoxy radical.

The term "$(C_3-C_7)$cycloalkyl" means a cyclic alkyl group of 3 to 7 carbon atoms, such as a cyclopropyl, cyclobutyl, cyclopentyl, cyclohexyl or cycloheptyl group.

Among the compounds of formula (I) that comprise subjects of the invention, a first group consists of the compounds for which:

Ar represents a phenyl di-substituted with a halogen atom;

and/or $R_1$ represents a phenyl that is unsubstituted or substituted once or twice with a halogen atom;

and/or $R_2$ represents:
  a pyridyl;
  a phenyl that is unsubstituted or substituted once or twice with one or two substituents independently chosen from a halogen atom, a $(C_1-C_4)$alkyl, a $(C_1-C_4)$ alkoxy, a tri-fluoromethyl group and a tri-fluoromethoxy group;
  $R_2$ may also represent a heterocyclic radical chosen from azetidine, pyrrolidine, piperidine, morpholine, thiomorpholine and perhydroazetidine when $R_3$ represents a group —$CONR_{11}R_{12}$;

and/or $R_3$ represents a group chosen from:
  (5) —$(CH_2)_q$—OH in which q is 0;
  (10) —$(CH_2)_q$—$NR_7COR_8$ in which q is 0;
  (11) —$(CH_2)_q$—$NR_7COOR_9$ in which q is 0;
  (18) —$CON_{11}R_{12}$;

$R_7$, $R_8$, $R_9$, $R_{11}$ and $R_{12}$ being as defined for a compound of formula (I) in the form of its' base or acid-addition salt, and also in the form of its' hydrate or solvate.

Among the compounds of the latter group, these include compounds of formula (I) for which:

Ar represents a phenyl disubstituted with a halogen atom;

$R_1$ represents a phenyl that is unsubstituted or substituted once or twice with a halogen atom;

$R_2$ represents:
  a pyridyl;
  a phenyl that is un-substituted once or twice with one or two substituents independently chosen from a halogen atom, a $(C_1-C_4)$alkyl, a $(C_1-C_4)$alkoxy, a tri-fluoromethyl group and a tri-fluoromethoxy group;
  $R_2$ may also represent a heterocyclic radical chosen from azetidine, pyrrolidine, piperidine, morpholine, thiomorpholine and perhydroazetidine when $R_3$ represents a group —$CONR_{11}R_{12}$;

$R_3$ represents a group chosen from:
  (5) —$(CH_2)_q$—OH in which q is 0;
  (10) —$(CH_2)_q$—$NR_7COR_8$ in which q is 0;
  (11) —$(CH_2)_q$—$NR_7COOR_9$ in which q is 0;
  (18) —$CONR_{11}R_{12}$;

$R_7$, $R_8$, $R_9$, $R_{11}$ and $R_{12}$ being as defined for a compound of formula (I) in the form of its' base or of acid-addition salt, and also in the form of its' hydrate or solvate.

Among the latter compounds, these also include compounds of formula (I) for which:

Ar represents a 3,4-dichlorophenyl or a 3,4-difluorophenyl;

$R_1$ represents a phenyl, a 4-chlorophenyl, a 4-fluorophenyl or a 3,4-difluorophenyl;

$R_2$ represents:
  a 2-pyridyl;
  a phenyl, a 4-chlorophenyl, a 3-fluorophenyl, a 4-fluorophenyl, a 3,4-difluorophenyl, a 3-methylphenyl, a 3,4-dimethylphenyl, a 4-methoxyphenyl, a 3-(trifluoromethyl)phenyl, a 4-(trifluoromethyl)phenyl or a 4-(trifluoromethoxy)phenyl;
  $R_2$ may also represent a 1-piperidyl when $R_3$ represents a —$CONH_2$ group or a —$CON(CH_3)_2$ group;

$R_3$ may also represent a group chosen from:
  a hydroxyl;

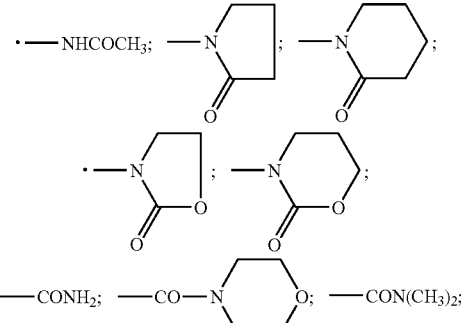

in the form of its' base or its' acid-addition salt, and also in the form of its' hydrate or solvate.

Moreover, among the compounds of formula (I) that are subjects of the invention, these also particularly include the following compounds:

6-(3,4-dichlorophenyl)-6-[2-[4-hydroxy-4-[3-(trifluoromethyl)phenyl]-1-piperidyl]ethyl]-4-phenylmorpholin-3-one and its' dextrorotatory isomer;

N-[1-[2-[2-(3,4-dichlorophenyl)-5-oxo-4-phenylmorpholin-2-yl]ethyl]-4-phenyl-4-piperidyl]-acetamide and its' dextrorotatory isomer;

N-[1-[2-[2-(3,4-dichlorophenyl)-5-oxo-4-phenylmorpholin-2-yl]ethyl]-4-(3-fluorophenyl)-4-piperidyl]acetamide and its' dextrorotatory isomer;

N-[1-[2-[2-(3,4-dichlorophenyl)-5-oxo-4-phenylmorpholin-2-yl]ethyl]-4-(3,4-difluorophenyl)-4-piperidyl]acetamide and its' dextrorotatory isomer;

N-[1-[2-[2-(3,4-dichlorophenyl)-5-oxo-4-phenylmorpholin-2-yl]ethyl]-4-(4-methylphenyl)-4-piperidyl]acetamide and its' dextrorotatory isomer;

N-[1-[2-[2-(3,4-dichlorophenyl)-5-oxo-4-phenylmorpholin-2-yl]ethyl]-4-(4-methoxyphenyl)-4-piperidyl]acetamide and its' dextrorotatory isomer;

N-[1-[2-[2-(3,4-dichlorophenyl)-5-oxo-4-phenylmorpholin-2-yl]ethyl]-4-(4-(trifluoromethoxy)-phenyl]-4-piperidyl]acetamide and its' dextrorotatory isomer;

6-(3,4-dichlorophenyl)-6-[2-[4-(3-fluoro-phenyl)-4-(2-oxopyrrolidin-1-yl)-1-piperidyl]ethyl]-4-phenylmorpholin-3-one, and its' dextrorotatory isomer;

6-(3,4-dichlorophenyl)-6-[2-[4-(3,4-di-fluorophenyl)-4-(2-oxopyrrolidin-1-yl)-1-piperidyl]-ethyl]-4-phenylmorpholin-3-one, and its' dextrorotatory isomer;

6-(3,4-dichlorophenyl)-6-[2-[4-(4-methyl-phenyl)-4-(2-oxopyrrolidin-1-yl)-1-piperidyl]ethyl]-4-phenylmorpholin-3-one, and its' dextrorotatory isomer;

1'-[2-[2-(3,4-dichlorophenyl)-5-oxo-4-phenylmorpholin-2-yl]ethyl]-4'-(4-methylphenyl)-1,4'-bipiperidin-2-one, and its' dextrorotatory isomer;

6-(3,4-dichlorophenyl)-6-[2-[4-(3-methyl-phenyl)-4-(2-oxopyrrolidin-1-yl)-1-piperidyl]ethyl]-4-phenylmorpholin-3-one, and its' dextrorotatory isomer;

6-(3,4-dichlorophenyl)-6-[2-[4-(3-fluoro-phenyl)-4-(2-oxo-1,3-oxazolidin-3-yl)-1-piperidyl]-ethyl]-4-phenylmorpholin-3-one, and its' dextrorotatory isomer;

6-(3,4-dichlorophenyl)-6-[2-[4-(4-fluoro-phenyl)-4-(2-oxo-1,3-oxazolidin-3-yl)-1-piperidyl]-ethyl]-4-phenylmorpholin-3-one, and its' dextrorotatory isomer;

6-(3,4-dichlorophenyl)-6-[2-[4-(3,4-dimethyl-phenyl)-4-(2-oxo-1,3-oxazolidin-3-yl)-1-piperidyl]-ethyl]-4-phenylmorpholin-3-one, and its' dextrorotatory isomer;

3-[1-[2-[2-(3,4-dichlorophenyl)-5-oxo-4-phenylmorpholin-2-yl]ethyl]-4-phenyl-4-piperidyl]-1,3-oxazinan-2-one, and its' dextrorotatory isomer;

3-[1-[2-[2-(3,4-dichlorophenyl)-5-oxo-4-phenylmorpholin-2-yl]ethyl]-4-(4-fluorophenyl)-4-piperidyl]-1,3-oxazinan-2-one, and its' dextrorotatory isomer;

3-[1-[2-[2-(3,4-dichlorophenyl)-5-oxo-4-phenylmorpholin-2-yl]ethyl]-4-(3,4-difluorophenyl)-4-piperidyl]-1,3-oxazinan-2-one, and its' dextrorotatory isomer;

-6-(3,4-dichlorophenyl)-6-[2-[4-(morpholin-4-ylcarbonyl)-4-phenyl-1-piperidyl]ethyl]-4-phenylmorpholin-3-one, and its' dextrorotatory isomer;

-1'-[2-[2-(3,4-dichlorophenyl)-5-oxo-4-phenylmorpholin-2-yl]ethyl]-1,4'-bipiperidin-4'-carboxamide, and its' dextrorotatory isomer;

-6-(3,4-dichlorophenyl)-6-[2-[4-(3,4-di-fluorophenyl)-4-(2-oxo-1,3-oxazolidin-3-yl)-1-piperidyl]ethyl]-4-phenylmorpholin-3-one, dextrorotatory and its' isomer;

N-[1-[2-[2-(3,4-dichlorophenyl)-5-oxo-4-phenylmorpholin-2-yl]ethyl]-4-phenyl-4-piperidyl]-acetamide, and its' dextrorotatory isomer;

N-[1-[2-[2-(3,4-dichlorophenyl)-5-oxo-4-phenylmorpholin-2-yl]ethyl]-4-[4-(trifluoromethyl)-phenyl]-4-piperidyl]acetamide, and its' dextrorotatory isomer;

1'-[2-[2-(3,4-difluorophenyl)-5-oxo-4-phenylmorpholin-2-yl]ethyl]-1,4'-bipiperidine-4'-carboxamide, and its' dextrorotatory isomer;

N-[1-[2-[2-(3,4-dichlorophenyl)-5-oxo-4-phenylmorpholin-2-yl]ethyl]-4-[3-(trifluoromethyl)-phenyl]-4-piperidyl] acetamide, and its' dextrorotatory isomer;

6-(3,4-dichlorophenyl)-6-[2-(4-hydroxy-4-pyridin-2-yl-1-piperidyl)ethyl]-4-phenylmorpholin-3-one, and its' dextrorotatory isomer;

N-[1-[2-[4-(4-chlorophenyl)-2-(3,4-dichloro-phenyl)-5-oxomorpholin-2-yl]ethyl]-4-phenyl-4-piperidyl]acetamide;

4-(4-chlorophenyl)-6-[2-[4-(4-chlorophenyl)-4-(2-oxo-1,3-oxazolidin-3-yl)-1-piperidyl]ethyl]-6-(3,4-dichlorophenyl)morpholin-3-one;

1'-[2-[4-(4-chlorophenyl)-2-(3,4-dichloro-phenyl)-5-oxomorpholin-2-yl]ethyl]-N,N-dimethyl-1,4'-bipiperidine-4'-carboxamide;

4-[1-[2-[2-(3,4-dichlorophenyl)-4-(4-fluorophenyl)-5-oxomorpholin-2-yl]ethyl]-4-phenyl-4-piperidyl]acetamide;

N-[1-[2-[2-(3,4-dichlorophenyl)-4-(4-fluorophenyl)-5-oxomorpholin-2-yl]ethyl]-4-(3,4-difluoro-phenyl)-4-piperidyl]acetamide;

-1'-[2-[2-(3,4-dichlorophenyl)-4-(4-fluoro-phenyl)-5-oxomorpholin-2-yl]ethyl]-N,N-dimethyl-1,4'-bipiperidine-4'-carboxamide;

—N-[1-[2-[2-(3,4-dichlorophenyl)-4-(3,4-di-fluorophenyl)-5-oxomorpholin-2-yl]ethyl]-4-phenyl-4-piperidyl]acetamide;

in the form of their base or acid-addition salt, and also in the form of their hydrate or solvate.

The present invention also comprises the following compounds including:

N-[1-[2-[2-(3,4-dichlorophenyl)-5-oxo-4-phenylmorpholin-2-yl]ethyl]-4-(3-fluorophenyl)-4-piperidyl]acetamide, and its' dextrorotatory isomer both in the form of their base or acid-addition salt, hydrate or solvate, is preferred.

In the following text, the term "protecting group Pg" means a group that allows a reactive function such as a hydroxyl or an amine to be protected during a synthesis, and, secondly, allows the intact reactive function to be regenerated at the end of the synthesis. Examples of protecting groups and of protection and de-protection methods are described in "Protective Groups in Organic Synthesis", Green et al., 2nd edition (John Wiley & Sons, Inc., New York), 1991.

Also, the term "leaving group" means a group that can be readily cleaved from a molecule by splitting a heterolytic bond, with the loss of an electron pair. This group may thus be readily replaced with another group during a substitution reaction such as halogens or an activated hydroxyl group such as a methanesulfonate, benzenesulfonate, p-toluenesulfonate, triflate, acetate, etc. Examples of leaving groups and references for preparing them are given in "Advanced in Organic Chemistry", J. March, 3rd edition, Wiley Interscience, 1985, p. 310-316.

In accordance with the present invention, the compounds of formula (I) may be prepared according to a process comprising:

A compound of formula:

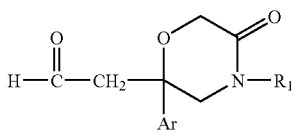

(II)

in which Ar and $R_1$ are as defined previously for formula (I), is reacted with a compound of formula:

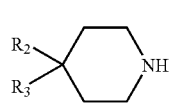

(III)

in which $R_2$ and $R_3$ are as defined previously for formula (I), in the presence of an acid, in a solvent, and the intermediate aminium salt formed is then reduced using a reducing agent.

The compound of formula (I) is optionally converted into an acid-addition salt thereof.

The reaction is performed in the presence of an acid such as acetic acid, in a solvent such as methanol or dichloromethane, at a temperature of between room temperature and the reflux point of the solvent, and forms in-situ an intermediate imine that is reduced chemically using, for example, sodium cyanoborohydride or sodium triacetoxyborohydride, or reduced catalytically using hydrogen and a catalyst such as palladium-on-charcoal or Raney nickel®.

According to one variant of the process:
a compound of formula:

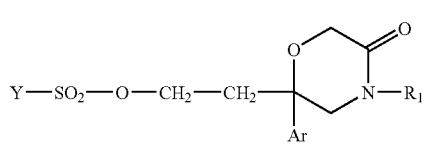

(IV)

in which Ar and $R_1$ are as defined for a compound of formula (I), and Y represents a methyl, phenyl, tolyl or trifluoromethyl group, is reacted with a compound of formula:

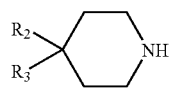

(III)

in which $R_2$ and $R_3$ are as defined previously for formula (I).

Optionally, the compound of formula (I) is converted into an acid-addition salt thereof.

The reaction is performed in a solvent such as N,N-dimethylformamide, acetonitrile, dichloromethane, toluene or 2-propanol and in the presence or absence of a base. When a base is used, it is chosen from organic bases such as triethylamine, N,N-diisopropylethylamine or N-methylmorpholine or from alkali metal carbonates or bicarbonates such as potassium carbonate, sodium carbonate or sodium bicarbonate. In the absence of a base, the reaction is performed using an excess of the compound of formula (III) and in the presence of an alkali metal iodide such as potassium iodide or sodium iodide. The reaction is performed at a temperature of between room temperature and 100° C.

The compound of formula (I) thus obtained may be subsequently separated from the reaction medium and purified according to the standard methods, for example by crystallization or chromatography.

The compounds of formula (II) are prepared by oxidation of the compounds of formula:

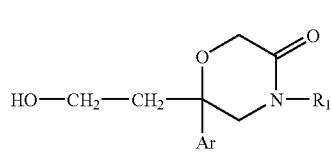

(V)

in which Ar and $R_1$ are as defined for a compound of formula (I).

The oxidation reaction is performed using, for example, oxalyl chloride, dimethyl sulfoxide and tri-ethylamine in a solvent such as dichloromethane and at a temperature of between −78° C. and room temperature.

The compounds of formula (V) are prepared by de-protection of the compounds of formula:

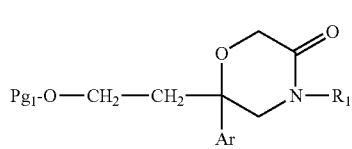

(VI)

in which Ar and $R_1$ are as defined for a compound of formula (I) and $Pg_1$ represents a standard O-protecting group, for instance 2-tetrahydropyranyl, benzoyl or a ($C_1$-$C_4$) alkylcarbonyl.

The de-protection is performed according to the standard methods that are well known to those skilled in the art. For example, when $Pg_1$ represents a 2-tetrahydropyranyl group, the de-protection is performed by acid hydrolysis using hydrochloric acid in a solvent such as ether, methanol or a mixture of these solvents, or using pyridinium p-toluenesulfonate in a solvent such as methanol, or alternatively by using an Amberlyst® resin in a solvent such as methanol. The reaction is performed at a temperature of between room temperature and the reflux point of the solvent. When $Pg_1$ represents a benzoyl group or a ($C_1$-$C_4$)alkylcarbonyl group, the de-protection is performed by hydrolysis in alkaline medium using, for example, an alkali metal hydroxide such as sodium hydroxide, potassium hydroxide or lithium hydroxide, in a solvent such as water, methanol, ethanol, dioxane or a mixture of these solvents, at a temperature of between 0° C. and the reflux point of the solvent.

The compounds of formula (VI) are prepared by cyclization of the compounds of formula VII:

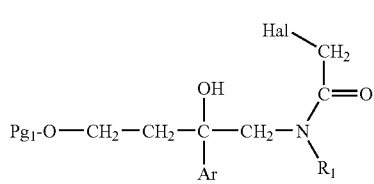
(VII)

in which Ar and $R_1$ are as defined previously for compound (I), $Pg_1$ is as defined previously for compound (VI) and Hal represents a halogen atom, preferably chlorine or bromine. The cyclization reaction is performed in the presence of a base such as potassium tert-butoxide in a solvent such as tetra-hydrofuran and at a temperature of between −60° C. and room temperature.

The compounds of formula (VII) are prepared by reacting a compound of formula VIII:

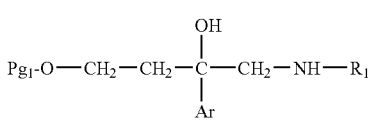
(VIII)

in which Ar and $R_1$ are as defined for formula (I) and $Pg_1$ is as defined for formula (VI), with a compound of formula Hal'-CO—$CH_2$-Hal in which Hal and Hal' represent a halogen atom, preferably chlorine or bromine, in the presence of a base such as triethylamine, N-methylmorpholine or pyridine. The reaction is performed in a solvent such as dichloromethane, 1,2-dichloroethane, tetrahydrofuran, dioxane or N,N-dimethylformamide, at a temperature of between −70° C. and room temperature.

The compounds of formula (VIII) are prepared by reacting the compounds of formula IX:

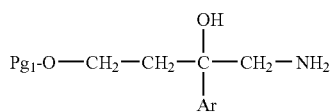
(IX)

in which Ar is as defined for a compound of formula (I) and $Pg_1$ is as defined for a compound of formula (VI), with a compound of formula X:

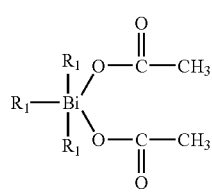
(X)

in which $R_1$ is as defined previously for formula (I), in the presence of copper(II) dipivaloate according to the amine arylation methods described in Tetrahedron, 1997, 53 (12), 4137-4144; Tetrahedron Letters, 1996, 37 (19), 3295-3298; Tetrahedron, 1998, 54, 4313-4318 which is hereby incorporated by reference.

The compounds of formula (IX) are known and are prepared according to the methods described in WO 96/23787 or in WO 00/58292.

The compounds of formula (X) are prepared from the triarylbismuthane of formula XI:

(XI)

in which $R_1$ is as defined for a compound of formula (I), according to known methods such as those described in Synthetic Communications, 1996, 26 (24), 4569-4575 or in the literature cited above for the arylation reaction.

The compounds of formula (XI) are commercial or are prepared according to the methods described in Synthetic Communications, 1996, 26 (24), 4569-4575.

The compounds of formula (III) are known or are prepared according to known methods such as those described in EP-0 428 434, EP-0 512 901, EP-0 515 240, WO 96/23787, WO 02/094821 and WO 03/104225.

The compounds of formula (III) are generally prepared in protected form on the nitrogen atom of the piperidine; after a deprotection step, the expected compounds of formula (III) are obtained.

In particular, the compounds of formula (III) in which $R_3$ represents a group —$(CH_2)_q$—$NR_7COR_8$ in which $R_7$ and $R_8$ together represent a group —$(CH_2)_p$— are prepared according to Scheme I below, in which $Pg_2$ represents an N-protecting group such as a benzyl, a benzyloxycarbonyl or a tert-butyloxycarbonyl, Hal represents a halogen atom, preferably chlorine, and $R_2$, q and p are as defined for a compound of formula (I).

Scheme I

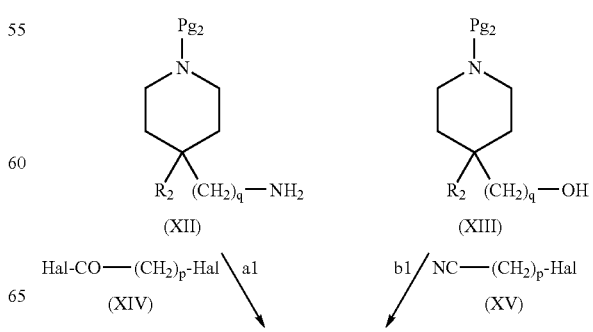

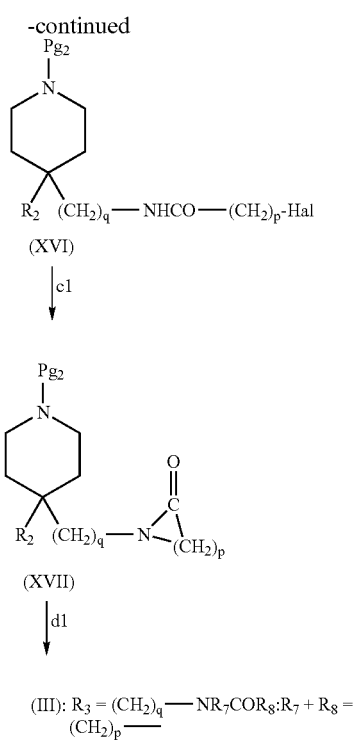

In step a1 of Scheme I, a compound of formula (XII) is reacted with a compound of formula (XIV) in the presence of a base such as triethylamine, in a solvent such as acetonitrile or dichloromethane and at a temperature of between 0° C. and room temperature, to give a compound of formula (XVI).

A compound of formula (XVI) may also be obtained by reacting, in step b1, a compound of formula (XIII) with a compound of formula (XV), in the presence of a strong acid such as sulfuric acid, without solvent and at a temperature of between 0 and 5° C.

The cyclization, in step c1, of the compound of formula (XVI) to give the compound of formula (XVII) is performed in the presence of a base such as sodium hydride, in a solvent such as N,N-dimethylformamide and at a temperature of between room temperature and 60° C.

The compound of formula (XVII) is deprotected in step d1 according to the known methods to give the expected compounds of formula (III).

The compounds of formula (III) in which $R_3$ represents a group $-(CH_2)_q-NR_7COOR_9$ in which $R_7$ and $R_9$ together represent a group $-(CH_2)_n-$ are prepared according to Scheme II below, in which $Pg_2$ represents an N-protecting group as defined above, Hal represents a halogen atom, preferably chlorine, and $R_2$, q and n are as defined for formula (I).

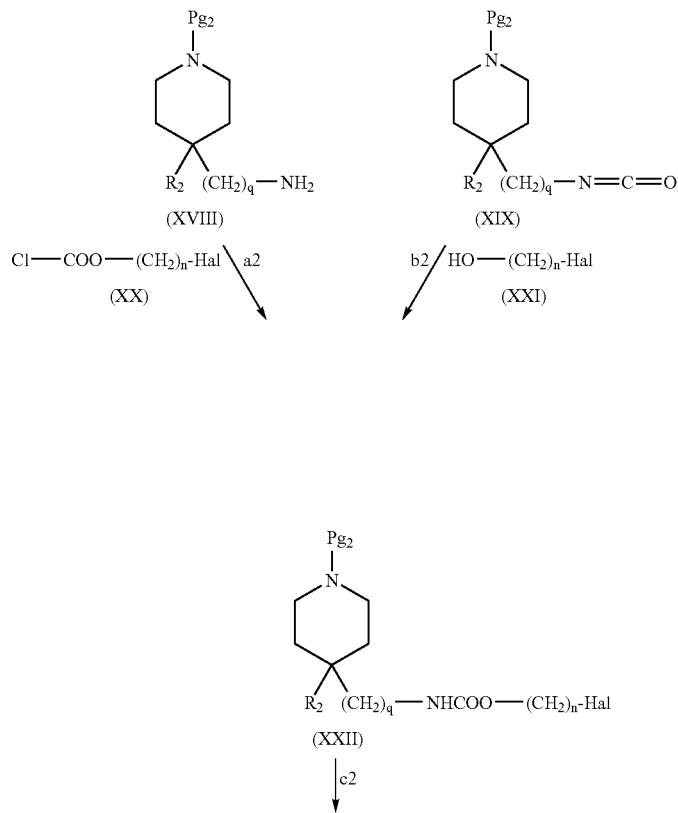

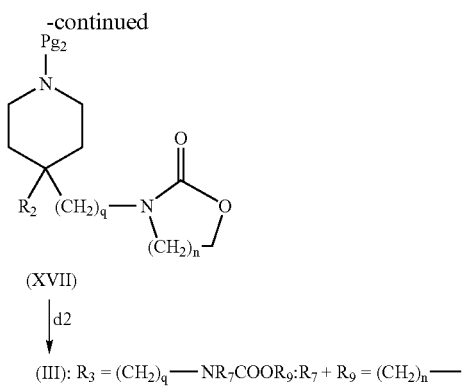

(XVII)

↓ d2

(III): $R_3 = (CH_2)_q-NR_7COOR_9 : R_7 + R_9 = (CH_2)_n-$

In step a2 of Scheme II, a compound of formula (XVIII) is reacted with a compound of formula (XX) in the presence of a base such as triethylamine, in a solvent such as dichloromethane or 1,2-dichloroethane and at a temperature of between 0° C. and room temperature, to obtain a compound of formula (XXII).

A compound of formula (XXII) may also be obtained by reacting, in step b2, a compound of formula (XIX) with a compound of formula (XXI) in a solvent such as 1,2-dichloroethane and at the reflux point of the solvent.

The compound of formula (XXIII) is deprotected in step d2 according to the standard methods to give the expected compound of formula (III).

The compounds of formula (III) in which $R_3$ represents a group $-(CH_2)_q-NR_7CONR_{11}R_{12}$ in which $R_7$ and $R_{12}$ together represent a group $-(CH_2)_m-$ is prepared according to Scheme III below, in which $Pg_2$ represents an N-protecting group as defined above, Hal represents a halogen atom, preferably chlorine, and $R_2$, q and m are as defined for a compound of formula (I).

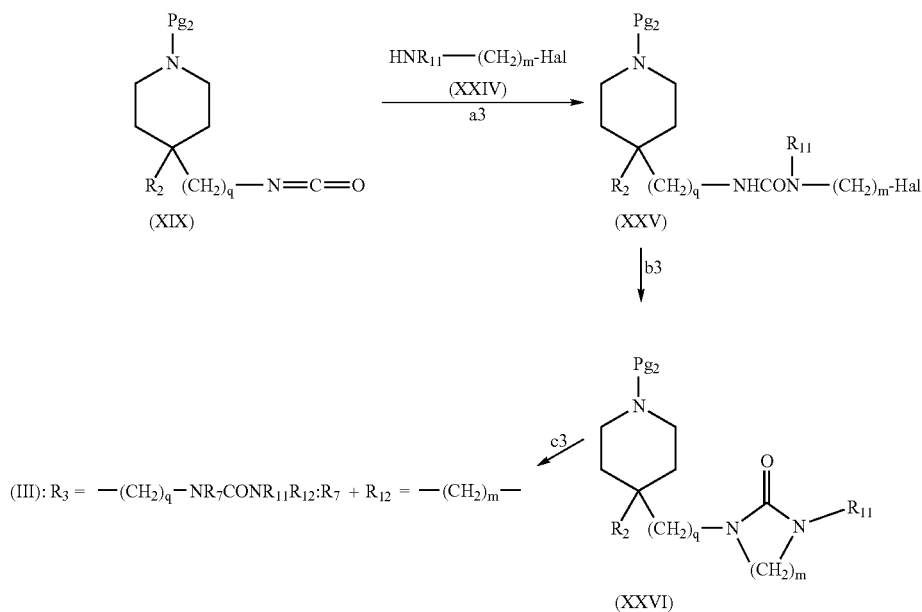

Scheme III (III): $R_3 = -(CH_2)_q-NR_7CONR_{11}R_{12} : R_7 + R_{12} = -(CH_2)_m-$ The compound of formula (XIX) is obtained by the action of sodium azide on the corresponding acid chloride according to the method described in Organic Syntheses, 51, 48-52.

The cyclization, in step c2, of the compound of formula (XXII) to give the compound of formula (XXIII) is performed in the presence of a base such as sodium hydride, in a solvent such as N,N-dimethylformamide and at a temperature of between room temperature and 60° C.

In step a3 of Scheme III, a compound of formula (XIX) is reacted with a compound of formula (XXIV) in a solvent such as 1,2-dichloroethane and at a temperature of between room temperature and the reflux point of the solvent.

The cyclization, in step b3, of the compound of formula (XXV) to give the compound of formula (XXVI) is performed in the presence of a base such as sodium hydride, in a solvent such as N,N-dimethylforamide and at a temperature of between room temperature and 60° C.

The compound of formula (XXVI) is deprotected in step c3 according to the standard methods to give the expected compound of formula (III).

The compounds of formula (IV) are prepared by reacting a compound of formula (V) with a compound of formula:

$$Y\text{---}SO_2\text{---}Cl \qquad (XXVII)$$

in which Y represents a methyl, phenyl, tolyl or trifluoromethyl group, in the presence of a base such as triethylamine, N,N-diisopropylethylamine or pyridine, in a solvent such as dichloromethane or toluene, and at a temperature of between −20° C. and the reflux point of the solvent.

According to another of its aspects, a subject of the invention is also the group of compounds of formulae (II), (IV), (V), (VI), (VII) or (VIII) and certain compounds of formula (III). These compounds are useful as intermediates for the synthesis of the compounds of formula (I). Thus, one aspect of the invention are compounds of formula:

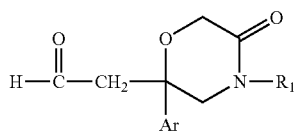
(II)

in which:
Ar represents a phenyl that is mono- or di-substituted with a halogen atom;
$R_1$ represents a phenyl that is unsubstituted or substituted once or twice with one or two substituents independently chosen from a halogen atom, a $(C_1\text{-}C_4)$alkyl and a $(C_1\text{-}C_4)$alkoxy.

A subject of the invention is also compounds of formula:

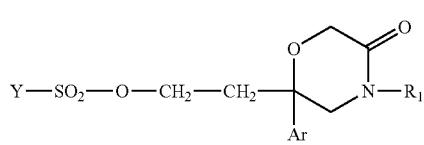
(IV)

in which:
Y represents a methyl, phenyl, tolyl or trifluoromethyl group;
Ar represents a phenyl that is mono- or disubstituted with a halogen atom;
$R_1$ represents a phenyl that is unsubstituted or substituted once or twice with one or two substituents independently chosen from a halogen atom, a $(C_1\text{-}C_4)$alkyl and a $(C_1\text{-}C_4)$alkoxy.

A subject of the invention is also compounds of formula:

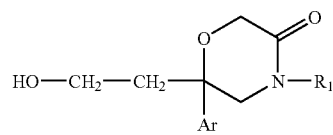
(V)

in which:
Ar represents a phenyl that is mono- or disubstituted with a halogen atom;
$R_1$ represents a phenyl that is unsubstituted or substituted once or twice with one or two substituents independently chosen from a halogen atom, a $(C_1\text{-}C_4)$alkyl and a $(C_1\text{-}C_4)$alkoxy.

A subject of the invention is also compounds of formula:

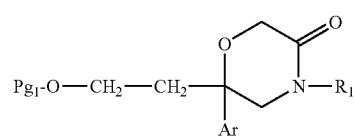
(VI)

in which:
$Pg_1$ represents a 2-tetrahydropyranyl, benzoyl or $(C_1\text{-}C_4)$ alkylcarbonyl radical;
Ar represents a phenyl that is mono- or disubstituted with a halogen atom;
$R_1$ represents a phenyl that is unsubstituted or substituted once or twice with one or two substituents independently chosen from a halogen atom, a $(C_1\text{-}C_4)$alkyl and a $(C_1\text{-}C_4)$alkoxy.

A subject of the invention is also compounds of formula:

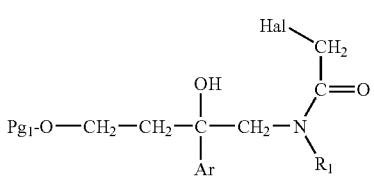
(VII)

in which:
Hal represents a chlorine or bromine atom;
$Pg_1$ represents a 2-tetrahydropyranyl, benzoyl or $(C_1\text{-}C_4)$ alkylcarbonyl radical;
Ar represents a phenyl that is mono- or disubstituted with a halogen atom;
$R_1$ represents a phenyl that is unsubstituted or substituted once or twice with one or two substituents independently chosen from a halogen atom, a $(C_1\text{-}C_4)$alkyl and a $(C_1\text{-}C_4)$alkoxy.

A subject of the invention is also compounds of formula:

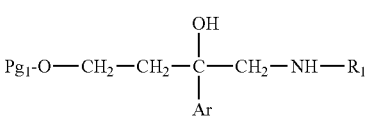
(VIII)

$Pg_1$ represents a 2-tetrahydropyranyl, benzoyl or $(C_1\text{-}C_4)$ alkylcarbonyl radical;
Ar represents a phenyl that is mono- or disubstituted with a halogen atom;
$R_1$ represents a phenyl that is unsubstituted or substituted once or twice with one or two substituents independently chosen from a halogen atom, a $(C_1\text{-}C_4)$alkyl and a $(C_1\text{-}C_4)$alkoxy.

A subject of the invention is also compounds of formula:

(III)

in which:
R$_2$ represents:
  a pyridyl;
  a phenyl that is unsubstituted or substituted once or twice with one or two substituents independently chosen from a halogen atom, a (C$_1$-C$_4$)alkyl, a (C$_1$-C$_4$) alkoxy, a trifluoromethyl group and a trifluoromethoxy group;
  a benzyl that is unsubstituted or substituted on the phenyl once or twice with one or two substituents independently chosen from a halogen atom, a (C$_1$-C$_4$) alkyl, a (C$_1$-C$_4$)alkoxy, a trifluoromethyl group and a trifluoromethoxy group;
R$_3$ represents a group:
  (11)-(CH$_2$)$_q$—NR$_7$COOR$_9$;
q is 0, 1 or 2;
R$_7$ and R$_9$ together represent a group —(CH$_2$)$_n$—;
n is 2 or 3;

in the form of base or of acid-addition salt.

Resolution of the racemic mixtures of the compounds of formula (I) allows the enantiomers to be isolated.

However, it is preferable to perform the resolution of the racemic mixtures using compounds of formula (IX) according to the methods described in WO 96/23787 or in WO 00/58292.

The examples that follow describe the preparation of certain compounds in accordance with the invention. These examples are not limiting and serve merely to illustrate the present invention. The numbers of the compounds given as examples refer to those given in Table (I) below, which illustrates the chemical structures and the physical properties of a number of compounds according to the invention.

In the Preparations and in the Examples, the following abbreviations are used:
ether: diethyl ether
iso ether: diisopropyl ether
DMSO: dimethyl sulfoxide
DMF: N,N-dimethylformamide
THF: tetrahydrofuran
DCM: dichloromethane
EtOAc: ethyl acetate
DIPEA: diisopropylethylamine
TFA: trifluoroacetic acid
BOP: benzotriazol-1-yloxytris(dimethylamino)-phosphonium hexafluorophosphate
2N hydrochloric ether: 2N solution of hydrogen chloride in diethyl ether
m.p.: melting point
rt: room temperature
b.p.: boiling point
HPLC: high performance liquid chromatography
silica H: 60H silica gel sold by Merck (Darmstadt)
pH 2 buffer solution: solution of 16.66 g of KHSO$_4$ and 32.32 g of K$_2$SO$_4$ in 1 liter of water.

The proton nuclear magnetic resonance spectra ($^1$H NMR) are recorded at 200 MHz in DMSO-d$_6$. The chemical shifts δ are expressed in parts per million (ppm). For the interpretation of the spectra, the following abbreviations are used: s: singlet, d: doublet, t: triplet, q: quartet: m: unresolved complex, mt: multiplet, bs: broad singlet, dd: doubled doublet.

The compounds according to the invention are analyzed by LC/UV/MS coupling (liquid chromatography/UV detection/mass spectrometry). The molecular peak (MH$^+$) and the retention time (tr) in minutes are measured.

A Symmetry C18 2.1×50 mm, 3.5 μm column is used, at 30° C., flow rate 0.4 ml/minute.

The eluent is composed as follows:
solvent A: 0.005% trifluoroacetic acid (TFA) in water at pH 3.15;
solvent B: 0.005% TFA in acetonitrile.
Gradient:

| Time (minutes) | % A | % B |
|---|---|---|
| 0 | 100 | 0 |
| 10 | 10 | 90 |
| 15 | 10 | 90 |
| 16 | 100 | 0 |
| 20 | 100 | 0 |

The UV detection is performed at λ=210 nm and the mass detection in positive ESI chemical ionization mode.

PREPARATIONS

1. Preparations of the Compounds of Formula (X)
   Preparation 1.1

Bis(acetato)triphenylbismuth (X):

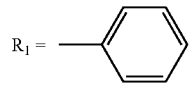

To a solution of 100 g of triphenylbismuthane in 720 ml of a DCM/THF mixture (70/30; v/v), 56.6 ml of a 32% solution of peracetic acid in acetic acid is added dropwise at rt and the mixture is then stirred for 2 hours. 200 ml of ether are added to the reaction mixture and the precipitate formed is filtered off by suction and washed with ether. 72.2 g of the expected product are obtained.

Preparation 1.2

Bis(acetato)tris(4-chlorophenyl)bismuth (X):

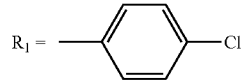

A) Tris(4-chlorophenyl)bismuthane

To a mixture of 2.54 g of magnesium covered with THF is added dropwise, at rt, a solution of 20 g of 1-bromo-4-chlorobenzene in 150 ml of THF is added dropwise at rt, and the mixture is refluxed for 1 hour. The reaction mixture is cooled to 0° C., and a solution of 9.9 g of BiCl₃ in 50 ml of THF is then added dropwise and the resulting mixture is refluxed for 1 hour and then stirred at rt overnight. The reaction mixture is poured into aqueous 10% NH₄Cl solution saturated with NaCl, filtered through Celite® and extracted with DCM. The organic phase is dried over MgSO₄ and the solvent is evaporated under vacuum. 15.5 g of the expected compound are obtained.

B) Bis(acetato)tris(4-chlorophenyl)bismuth

To a mixture of 13 g of the compound obtained in the preceding step (in 250 ml of acetic acid) 7.1 g of sodium perborate monohydrate is added and the mixture is stirred for 1 hour at rt. The reaction mixture is poured into 500 ml of water and extracted with DCM, the organic phase is washed with water and dried over MgSO₄, and the solvent is evaporated off under vacuum. 15.5 g of the expected compound are obtained.

Preparation 1.3

Bis(acetato)tris(4-fluorophenyl)bismuth (X):

$R_1 =$ 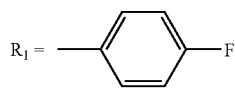 $-F$

A) Tris(4-fluorophenyl)bismuthane

To a mixture of 5.6 g of magnesium covered with THF is added, dropwise and at rt, a solution of 40 g of 1-bromo-4-fluorobenzene in 250 ml of THF, and the mixture is then refluxed for 1 hour. The reaction mixture is cooled to 0° C., a solution of 21.6 g of BiCl₃ in 100 ml of THF is added dropwise, and the resulting mixture is refluxed for 1 hour and stirred overnight at rt. The reaction mixture is poured into aqueous 10% NH₄Cl solution saturated with NaCl, filtered through Celite® and extracted with DCM, the organic phase is dried over MgSO₄ and the solvent is evaporated off under vacuum. 29.75 g of the expected compound are obtained.

B) Bis(acetato)tris(4-fluorophenyl)bismuth

To a mixture of 25 g of the compound obtained in the preceding step in 100 ml of acetic acid is added 2.3 g of sodium perborate tetrahydrate and the mixture is stirred for 1 hour at rt. The reaction mixture is poured into 1 liter of water and extracted with DCM, the organic phase is washed with water and dried over MgSO₄, and the solvent is evaporated off under vacuum. 27.34 g of the expected compound are obtained.

Preparation 1.4

Bis(acetato)tris(3,4-difluorophenyl)bismuth (X):

$R_1 =$ 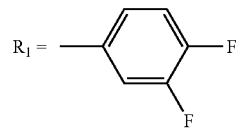

A) Tris(3,4-difluorophenyl)bismuthane

To a mixture of 2.5 g of magnesium covered with THF is added, dropwise at rt, a solution of 20 g of 1-bromo-3,4-difluorobenzene in 150 ml of THF, and the mixture is then refluxed for 1 hour. The reaction mixture is cooled to 0° C., a solution of 9.8 g of BiCl₃ in 50 ml of THF is added dropwise, and the resulting mixture is refluxed for 1 hour and then stirred overnight at rt. The reaction mixture is poured into aqueous 10% NH₄Cl solution saturated with NaCl, filtered through Celite® and extracted with DCM, the organic phase is dried over MgSO₄ and the solvent is evaporated off under vacuum. 15.75 g of the expected compound are obtained.

B) Bis(acetato)tris(3,4-difluorophenyl)bismuth

To a mixture of 13.5 g of the compound obtained in the preceding step in 250 ml of acetic acid is added 7.4 g of sodium perborate monohydrate and the mixture is stirred at rt for 1 hour. The reaction mixture is poured into 500 ml of water and extracted with DCM, the organic phase is washed with water and dried over MgSO₄, and the solvent is evaporated off under vacuum. 15.5 g of the expected compound are obtained.

2. Preparations of the Compounds of Formula (IX)

Preparation 2.1

4-Amino-3-(3,4-dichlorophenyl)-3-hydroxybutyl benzoate, laevorotatory isomer (IX):

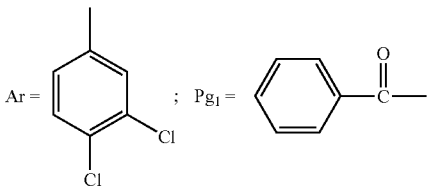

This compound is prepared according to the procedures described in steps A, B, C, D, E and F of Preparation 1.1 in WO 00/58292.

Preparation 2.2

4-Amino-3-(3,4-difluorophenyl)-3-hydroxybutyl benzoate, laevorotatory isomer (IX):

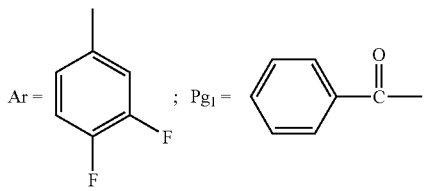

This compound is prepared according to the procedure described in step A of Preparation 1.16 in WO 96/23787.

Preparation 2.3

4-Amino-3-(3,4-dichlorophenyl)-3-hydroxybutyl benzoate (IX):

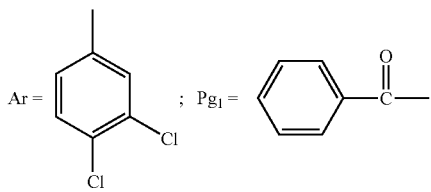

This compound is prepared according to the procedures described in steps A, B, C, D and E of Preparation 1.1 in WO 00/58292.

3. Preparations of the Compounds of Formula (VIII)

Preparation 3.1

4-Anilino-3-(3,4-dichlorophenyl)-3-hydroxybutyl benzoate, single isomer (VIII):

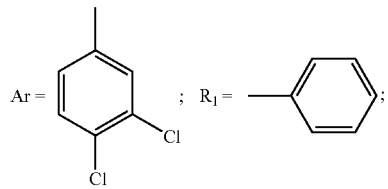

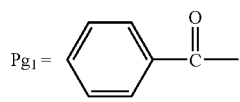

A) Copper(II) Dipivaloate

To a suspension of 13.6 g of $CuCO_3 \cdot Cu(OH)_2$ in 50 ml of water is added, dropwise at rt, a solution of 18.6 g of pivalic acid in 100 ml of hot water, and the mixture is stirred until the evolution of gas has ceased. The reaction mixture is filtered by suction and the precipitate is washed four times with water. The precipitate is taken up in 300 ml of THF, the insoluble material is filtered off and the filtrate is concentrated under vacuum. 7.2 g of the expected product are obtained after drying under vacuum.

B) 4-Anilino-3-(3,4-dichlorophenyl)-3-hydroxybutyl benzoate, single isomer

A mixture of 17.7 g of the compound obtained in Preparation 2.1, 30.7 g of the compound obtained in Preparation 1.1 and 1.25 g of the compound obtained in the preceding step in 960 ml of DCM is stirred overnight at rt. The reaction mixture is concentrated under vacuum, the residue is taken up in ether, the insoluble material is filtered off and the filtrate is concentrated under vacuum. The residue is chromatographed on silica H gel, eluting with DCM. 18.6 g of the expected product are obtained.

Preparation 3.2

4-Anilino-3-(3,4-difluorophenyl)-3-hydroxybutyl benzoate, single isomer (VIII):

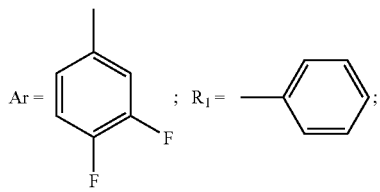

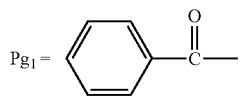

To a mixture of 0.5 g of the compound obtained in Preparation 2.2 and 0.04 g of the compound obtained in step A of Preparation 3.1 in 40 ml of DCM is added, at rt, 0.95 g of the compound obtained in Preparation 1.1, and the mixture is stirred at rt for 1 hour. The reaction mixture is acidified by adding a pH 2 buffer solution, neutralized to pH 7 by adding 10% $Na_2CO_3$ solution, the insoluble material is filtered off, the filtrate is separated out by settling of the phases, the organic phase is washed with water and dried over $Na_2SO_4$, and the solvent is evaporated off under vacuum. The residue is chromatographed on silica gel, eluting with DCM. 0.3 g of the expected product is obtained.

Preparation 3.3

4-[(4-Chlorophenyl)amino]-3-(3,4-dichlorophenyl)-
3-hydroxybutyl benzoate (VIII):

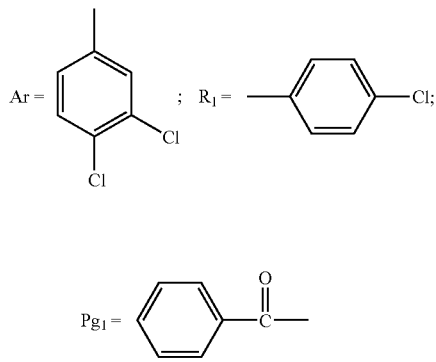

A mixture of 15.5 g of the compound obtained in Preparation 1.2, 8.3 g of the compound obtained in Preparation 2.3 and 0.62 g of the compound obtained in step A of Preparation 3.1 in 750 ml of DCM is stirred at rt for 18 hours. The reaction mixture is concentrated under vacuum, the residue is taken up in DCM, the insoluble material is filtered off and the filtrate is chromatographed on silica gel, eluting with DCM. 4.62 g of the expected compound are obtained.

Preparation 3.4

3-(3,4-Dichlorophenyl)-4-([(4-fluorophenyl)amino]-
3-hydroxybutyl benzoate (VIII):

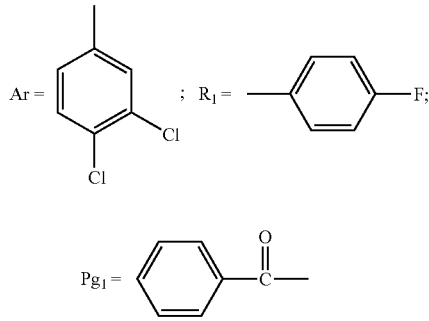

A mixture of 10 g of the compound obtained in Preparation 1.3, 5.78 g of the compound obtained in Preparation 2.3 and 0.43 g of the compound obtained in step A of Preparation 3.1 in 500 ml of DCM is stirred at rt for 18 hours. The reaction mixture is concentrated under vacuum, the residue is taken up DCM, the insoluble material is filtered off and the filtrate is chromatographed on silica gel, eluting with DCM. 5.84 g of the expected compound are obtained.

Preparation 3.5

3-(3,4-Dichlorophenyl)-4-[(3,4-difluorophenyl)-
amino]-3-hydroxybutyl benzoate (VIII):

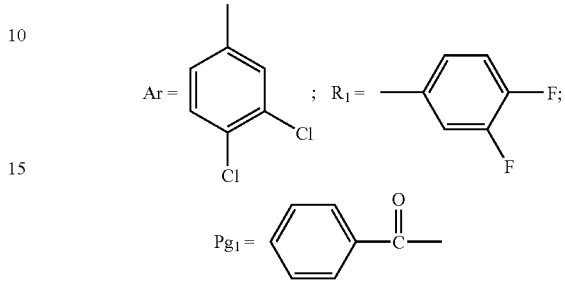

A mixture of 15.5 g of the compound obtained in Preparation 1.4, 8.2 g of the compound obtained in Preparation 2.3 and 0.62 g of the compound obtained in step A of Preparation 3.1 in 750 ml of DCM is stirred at rt for 18 hours. The mixture is concentrated under vacuum, the residue is taken up in DCM, the insoluble material is filtered off and the filtrate is chromatographed on silica gel, eluting with DCM. 5.42 g of the expected compound are obtained.

4. Preparations of the Compounds of Formula (VII)

Preparation 4.1

4-[(Chloroacetyl)(phenyl)amino]-3-(3,4-dichlorophenyl)-3-hydroxybutyl benzoate, laevorotatory
isomer (VII):

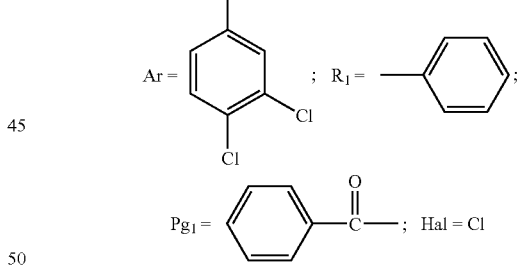

To a solution of 7.2 g of the compound obtained in Preparation 3.1 and 1.7 g of triethylamine in 100 ml of DCM is added, at rt, 1.9 g of chloroacetyl chloride, and the mixture is stirred at rt for 1 hour. A further 0.19 g of chloroacetyl chloride is added and the mixture is stirred at rt for 1 hour. The reaction mixture is concentrated under vacuum, the residue is extracted with EtOAc, the organic phase is washed with pH 2 buffer solution, with water and dried over $Na_2SO_4$, and the solvent is evaporated off under vacuum. 6.42 g of the expected product are obtained.

$$\alpha\frac{20}{D} = -119.9° \ (c = 1; \text{MeOH}).$$

Preparation 4.2

4-[(Chloroacetyl)(phenyl)amino]-3-(3,4-difluorophenyl)-3-hydroxybutyl benzoate, single isomer (VII):

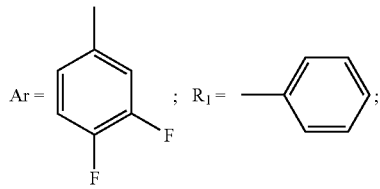

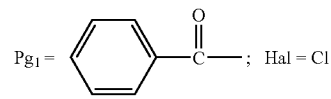

A mixture of 3.1 g of the compound obtained in Preparation 3.2 and 0.79 g of triethylamine in 60 ml of DCM is cooled to 0° C., a solution of 0.88 g of chloroacetyl chloride in 10 ml of DCM is added dropwise and the mixture is stirred for 2 hours. The reaction mixture is concentrated under vacuum, the residue is extracted with EtOAc, the organic phase is washed with pH 2 buffer solution, with water and dried over $Na_2SO_4$, and the solvent is evaporated off under vacuum. 3.5 g of the expected product are obtained.

Preparation 4.3

4-[(Chloroacetyl)(4-chlorophenyl)amino]-3-(3,4-dichlorophenyl)-3-hydroxybutyl benzoate (VII):

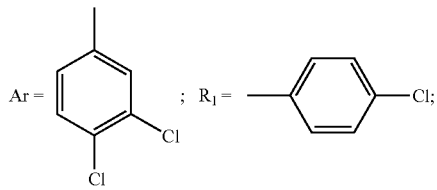

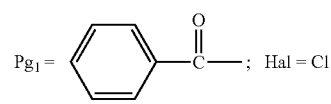

To a solution of 4.6 g of the compound obtained in Preparation 3.3 and 1 g of triethylamine in 150 ml of DCM is added 1.34 g of chloroacetyl chloride, and the mixture is stirred at rt overnight. The reaction mixture is concentrated under vacuum, the residue is extracted with EtOAc, the organic phase is washed with pH 2 buffer solution, with water, with saturated NaCl solution and dried over $MgSO_4$, and the solvent is evaporated off under vacuum. 5.25 g of the expected compound are obtained.

Preparation 4.4

4-[(Chloroacetyl)(4-fluorophenyl)amino]-3-(3,4-dichlorophenyl)-3-hydroxybutyl benzoate (VII):

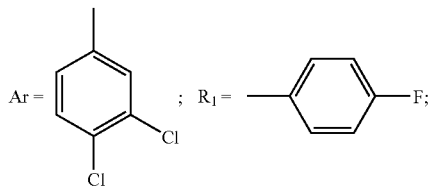

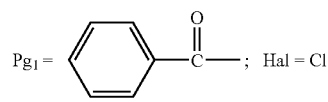

To a mixture of 8.5 g of the compound obtained in Preparation 3.4 and 2.64 ml of triethylamine in 150 ml of DCM is added 2.6 g of chloroacetyl chloride, and the mixture is stirred at rt overnight. The reaction mixture is concentrated under vacuum, the residue is extracted with EtOAc, the organic phase is washed with pH 2 buffer solution, with water, with saturated NaCl solution and dried over $MgSO_4$, and the solvent is evaporated off under vacuum. 9.5 g of the expected compound are obtained.

Preparation 4.5

4-[(Chloroacetyl)(3,4-difluorophenyl)amino]-3-(3,4-dichlorophenyl)-3-hydroxybutyl benzoate (VII):

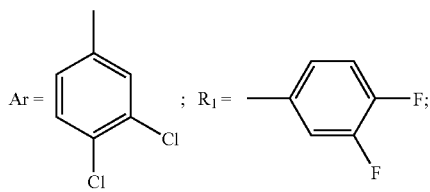

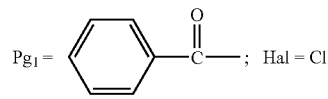

To a mixture of 5.4 g of the compound obtained in Preparation 3.5 and 1.17 g of triethylamine in 150 ml of DCM is added 1.57 g of chloroacetyl chloride, and the mixture is stirred at rt overnight. The reaction mixture is concentrated under vacuum, the residue is extracted with EtOAc, the organic phase is washed with pH 2 buffer solution, with water, with saturated NaCl solution and dried over $MgSO_4$, and the solvent is evaporated off under vacuum. 6.23 g of the expected compound are obtained.

5. Preparations of the Compounds of Formula (VI)

Preparation 5.1

2-[2-(3,4-Dichlorophenyl)-5-oxo-4-phenylmorpholin-2-yl]ethylbenzoate, single isomer (VI):

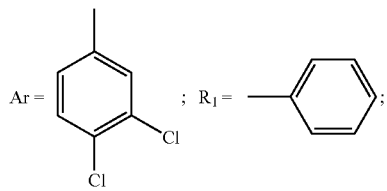

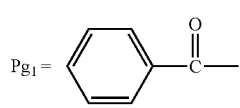

A solution of 16 g of the compound obtained in Preparation 4.1 in 750 ml of THF is cooled to −60° C., 3.54 g of potassium tert-butoxide are added, the temperature is allowed to rise to −30° C. with stirring, and is then left at −30° C. for 30 minutes with stirring. The reaction mixture is poured into a precooled pH 2 buffer solution and extracted with EtOAc, the organic phase is washed with water and dried over $Na_2SO_4$, and the solvent is evaporated off under vacuum. 14.85 g of the expected product are obtained.

Preparation 5.2

2-[2-(3,4-Difluorophenyl)-5-oxo-4-phenylmorpholin-2-yl]ethylbenzoate, single isomer (VI):

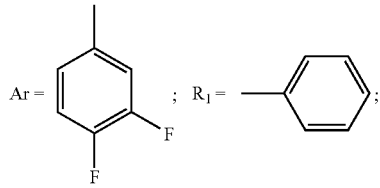

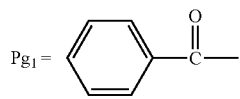

A solution of 3.5 g of the compound obtained in Preparation 4.2 in 120 ml of THF is cooled to −60° C., 1.75 g of potassium tert-butoxide are added and the mixture is stirred for 1 hour. The reaction mixture is poured into a pH 2 buffer solution and extracted with EtOAc, the organic phase is washed with water and dried over $Na_2SO_4$, and the solvent is evaporated off under vacuum. The expected product is obtained, and is used without further purification in Preparation 6.2.

Preparation 5.3

2-[4-(4-Chlorophenyl)-2-(3,4-dichlorophenyl)-5-oxomorpholin-2-yl]ethylbenzoate (VI):

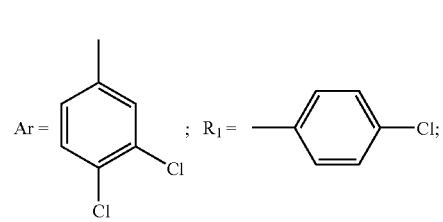

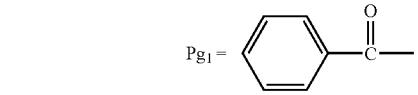

A solution of 1.28 g of potassium tert-butoxide in 250 ml of THF is cooled to −60° C., followed by dropwise addition of a solution of 6.2 g of the compound obtained in Preparation 4.3 in 40 ml of THF, the temperature is allowed to rise to −30° C. with stirring, and the mixture is stirred at −30° C. for 1 hour. The reaction mixture is poured into a precooled pH 2 buffer solution and extracted with EtOAc, the organic phase is washed with water, with saturated NaCl solution and dried over $MgSO_4$, and the solvent is evaporated off under vacuum. 5.8 g of the expected compound are obtained.

Preparation 5.4

2-[2-(3,4-Dichlorophenyl)-4-(4-fluorophenyl)-5-oxomorpholin-2-yl]ethylbenzoate (VI):

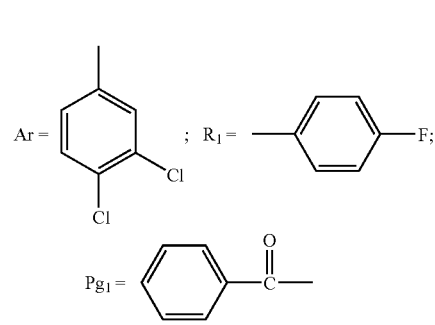

A solution of 2 g of potassium tert-butoxide in 450 ml of THF is cooled to −60° C., followed by dropwise addition of a solution of 9.5 g of the compound obtained in Preparation 4.4 in 40 ml of THF, the temperature is allowed to rise to −30° C. with stirring, and the mixture is stirred at −30° C. for 1 hour. The reaction mixture is poured into a precooled pH 2 buffer solution and extracted with EtOAc, the organic phase is washed with water, with saturated NaCl solution and dried over $MgSO_4$, and the solvent is evaporated off under vacuum. 8.4 g of the expected compound are obtained.

Preparation 5.5

2-[2-(3,4-Dichlorophenyl)-4-(3,4-difluorophenyl)-5-oxomorpholin-2-yl]ethylbenzoate (VI):

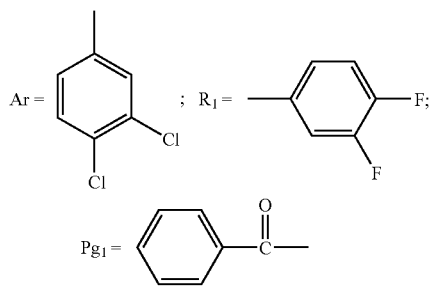

A solution of 1.08 g of potassium tert-butoxide in 250 ml of THF is cooled to −60° C., followed by dropwise addition of a solution of the compound obtained in Preparation 4.5 in 40 ml of THF, the temperature is allowed to rise to −30° C. with stirring, and the mixture is stirred at −30° C. for 1 hour. The reaction mixture is poured into a precooled pH 2 buffer solution and extracted with EtOAc, the organic phase is washed with water, with saturated NaCl solution and dried over MgSO$_4$, and the solvent is evaporated off under vacuum. 4.78 g of the expected compound are obtained.

6. Preparations of the Compounds of Formula (V)

Preparation 6.1

6-(3,4-Dichlorophenyl)-6-(2-hydroxyethyl)-4-phenylmorpholin-3-one, dextrorotatory isomer (V):

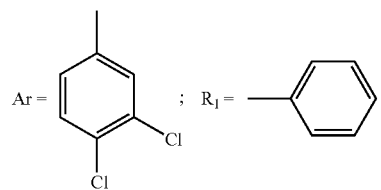

To a solution of 14.5 g of the compound obtained in Preparation 5.1 in 100 ml of MeOH is added, at rt, 0.74 g of lithium hydroxide monohydrate, and the mixture is stirred at rt for 1 hour. The reaction mixture is concentrated under vacuum, the residue is taken up in water and extracted with ether, the organic phase is washed with water and dried over Na$_2$SO$_4$, and the solvent is evaporated off under vacuum. The residue is chromatographed on silica H gel, eluting with DCM and then with a gradient of a DCM/MeOH mixture up to (98.5/1.5; v/v). 9 g of the expected product are obtained.

$$\alpha\frac{20}{D} = +96.6° \ (c = 1; \text{MeOH}).$$

Preparation 6.2

6-(3,4-Difluorophenyl)-6-(2-hydroxyethyl)-4-phenylmorpholin-3-one, single isomer (V):

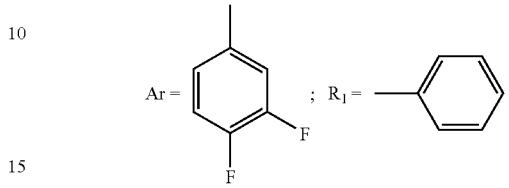

To a solution of the compound obtained in Preparation 5.2 in 30 ml of MeOH is added, at rt, 3 ml of concentrated NaOH solution, and the mixture is stirred at rt for 1 hour. The reaction mixture is concentrated under vacuum, the residue is taken up in water and extracted with EtOAc, the organic phase is washed with water and dried over Na$_2$SO$_4$, and the solvent is evaporated off under vacuum. The residue is chromatographed on silica H gel, eluting with a DCM/MeOH mixture (100/1; v/v). 1.3 g of the expected product are obtained.

Preparation 6.3

4-(4-Chlorophenyl)-6-(3,4-dichlorophenyl)-6-(2-hydroxyethyl)morpholin-3-one (V):

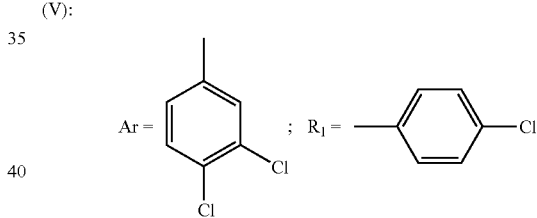

To a solution of 5.8 g of the compound obtained in Preparation 5.3 in 75 ml of MeOH is added, at rt, 0.48 g of lithium hydroxide monohydrate and 2 ml of water, and the mixture is then stirred at rt for 3 hours. The reaction mixture is concentrated under vacuum, the residue is taken up in water and extracted with ether, the organic phase is washed with water, with saturated NaCl solution and dried over MgSO$_4$, and the solvent is evaporated off under vacuum. 4.7 g of the expected compound are obtained.

Preparation 6.4

6-(3,4-Dichlorophenyl)-4-(4-fluorophenyl)-6-(2-hydroxyethyl)morpholin-3-one (V):

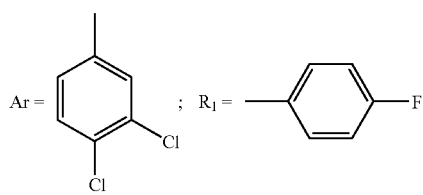

To a solution of 8.4 g of the compound obtained in Preparation 5.4 in 75 ml of MeOH is added 0.72 g of lithium hydroxide monohydrate and 2 ml of water, and the mixture is stirred at rt for 3 hours. The reaction mixture is concentrated under vacuum, the residue is taken up in water and extracted with ether, the organic phase is washed with water, with saturated NaCl solution and dried over MgSO$_4$, and the solvent is evaporated off under vacuum. 6.06 g of the expected compound are obtained.

Preparation 6.5

6-(3,4-Dichlorophenyl)-4-(3,4-difluorophenyl)-6-(2-hydroxyethyl)morpholin-3-one (V):

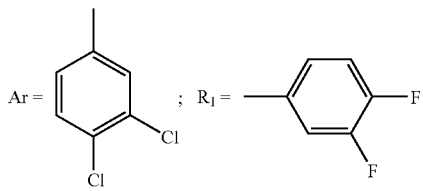

To a solution of 4.75 g of the compound obtained in Preparation 5.5 in 75 ml of MeOH is added 0.4 g of lithium hydroxide monohydrate and 2 ml of water, and the mixture is then stirred at rt for 3 hours. The reaction mixture is concentrated under vacuum, the residue is taken up in water and extracted with ether, the organic phase is washed with water, with saturated NaCl solution and dried over MgSO$_4$, and the solvent is evaporated off under vacuum. 3.8 g of the expected compound are obtained.

7. Preparations of the Compounds of Formula (II)

Preparation 7.1

[2-(3,4-Dichlorophenyl)-5-oxo-4-phenylmorpholin-2-yl]acetaldehyde, single isomer (II):

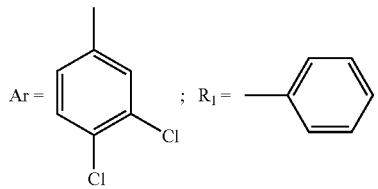

A solution of 1.6 g of the compound obtained in Preparation 6.1 and 18.6 ml of DMSO in 40 ml of DCM is cooled to −60° C., a solution of 1.1 g of oxalyl chloride in 20 ml of DCM is added dropwise and the mixture is stirred at −60° C. for 2 hours. 1.4 g of triethylamine are then added and the temperature is allowed to rise to rt with stirring. The reaction mixture is washed with 1N HCl solution and with water, the organic phase is dried over Na$_2$SO$_4$ and the solvent is evaporated off under vacuum. 1.6 g of the expected product are obtained.

Preparation 7.2

[2-(3,4-Difluorophenyl)-5-oxo-4-phenylmorpholin-2-yl]acetaldehyde, single isomer (II):

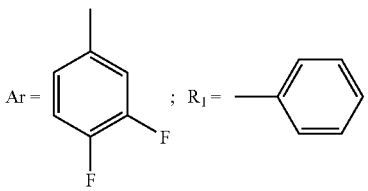

A solution of 1.14 g of oxalyl chloride in 20 ml of DCM is cooled to −70° C., a solution of 1.5 g of the compound obtained in Preparation 6.2 and 2.1 g of DMSO in 40 ml of DCM is added dropwise and the mixture is stirred for 3 hours at −70° C. 6.5 g of triethylamine are then added and the temperature is allowed to rise to rt with stirring. The reaction mixture is washed with 2N HCl solution and with water and dried over Na$_2$SO$_4$, and the solvent is evaporated off under vacuum. 1.4 g of the expected product are obtained.

Preparation 7.3

[4-(4-Chlorophenyl)-2-(3,4-dichlorophenyl)-5-oxo-morpholin-2-yl]acetaldehyde (II):

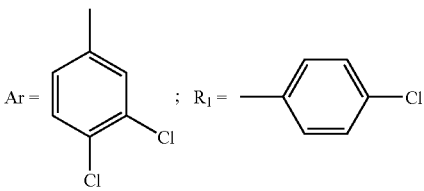

A solution of 2.05 ml of oxalyl chloride in 80 ml of DCM is cooled to −60° C., a solution of 2.50 ml of DMSO in 20 ml of DCM is added dropwise, followed by dropwise addition of a solution of 4.7 g of the compound obtained in Preparation 6.3 and 3.5 ml of DMSO in 40 ml of DCM, and the mixture is stirred at −60° C. for 1 hour. 10.1 ml of triethylamine are then added and the temperature is allowed to rise to rt with stirring. The reaction mixture is washed with 1N HCl solution, with 10% Na$_2$CO$_3$ solution and with saturated NaCl solution and dried over MgSO$_4$, and the solvent is evaporated off under vacuum. The residue is chromatographed on silica gel, eluting with DCM and then with a DCM/MeOH gradient of from (99/1; v/v) to (95/5; v/v). 2.58 g of the expected compound are obtained.

Preparation 7.4

[2-(3,4-Dichlorophenyl)-4-(4-fluorophenyl)-5-oxo-morpholin-2-yl]acetaldehyde (II):

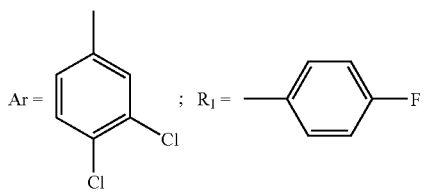

A mixture of 2.72 ml of oxalyl chloride in 80 ml of DCM is cooled to −60° C., a solution of 3.32 ml of DMSO in 20 ml of DCM is added dropwise, followed by dropwise addition of a solution of 6 g of the compound obtained in Preparation 6.4 and 4.65 ml of DMSO in 40 ml of DCM, and the mixture is stirred for 1 hour while cold. 13.5 ml of triethylamine are then added and the temperature is allowed to rise to rt with stirring. The reaction mixture is washed with 1N HCl solution, with 10% $Na_2CO_3$ solution and with saturated NaCl solution and dried over $MgSO_4$, and the solvent is evaporated off under vacuum. The residue is chromatographed on silica gel, eluting with DCM and then with a DCM/MeOH mixture gradient of from (99/1; v/v) to (95/5; v/v). 3.68 g of the expected compound are obtained.

Preparation 7.5

[2-(3,4-Dichlorophenyl)-4-(3,4-difluorophenyl)-5-oxomorpholin-2-yl]acetaldehyde (II):

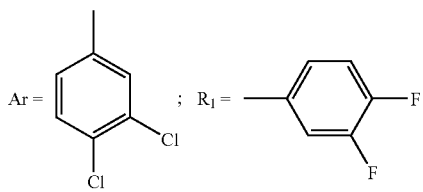

A mixture of 1.65 ml of oxalyl chloride in 80 ml of DCM is cooled to −60° C., a solution of 2 ml of DMSO in 20 ml of DCM is added dropwise, followed by dropwise addition of a solution of 3.8 g of the compound obtained in Preparation 6.5 and 2.8 ml of DMSO in 40 ml of DCM, and the mixture is stirred for 1 hour while cold. 8.15 ml of triethylamine are then added and the temperature is allowed to rise to RT with stirring. The reaction mixture is washed with 1N HCl solution, with 10% $Na_2CO_3$ solution and with saturated NaCl solution and dried over $MgSO_4$, and the solvent is evaporated off under vacuum. The residue is chromatographed on silica gel, eluting with a DCM/MeOH mixture gradient of from (99/1; v/v) to (95/5; v/v). 3 g of the expected compound are obtained.

8. Preparations of the Compounds of Formula (II)

Preparation 8.1

N-(4-Phenylpiperid-4-yl)acetamide (III):

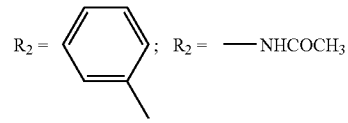

This compound is prepared according to the procedure described in EP 474 561.

Preparation 8.2

N-[4-(3-Fluorophenyl)piperid-4-yl]acetamide formate

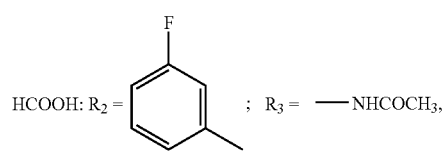

(III)

A) 1-Benzyl-4-(3-fluorophenyl)piperid-4-ol

To a suspension of 5.86 g of magnesium in 25 ml of THF is slowly added a solution of 42.16 g of 1-bromo-3-fluorobenzene in 100 ml of THF so as to reach and then maintain reflux of the THF, and the mixture is left at reflux for 1 hour with stirring. After cooling to rt, a solution of 38 g of 1-benzyl-4-piperidinone in 175 ml of THF is then added dropwise and the mixture is refluxed for 1 hour. After cooling to rt, the reaction mixture is poured into ice and extracted with EtOAc, the organic phase is washed with water and dried over $Na_2SO_4$, and the solvent is evaporated off under vacuum. 38 g of the expected product are obtained after crystallization from cyclohexane.

B) N-[1-Benzyl-4-(3-fluorophenyl)piperid-4-yl]acetamide

To a solution of 38 g of the compound obtained in the preceding step in 152 ml of acetonitrile is added dropwise, at a temperature below 30° C., 133 ml of 95% $H_2SO_4$ solution, and the mixture is then stirred for 3 hours at a temperature between 25 and 30° C. The reaction mixture is poured onto ice and basified by addition of concentrated NaOH solution, and the precipitate formed is filtered off by suction and washed with water. 42.8 g of the expected product are obtained after drying.

C) N-[4-(3-Fluorophenyl)piperid-4-yl]acetamide formate

A mixture of 14 g of the compound obtained in the preceding step, 16.32 g of ammonium formate and 2.3 g of 10% palladium-on-charcoal in 100 ml of ethanol is left at 40° C. for 30 minutes and then at rt for 1 hour 30 minutes. The catalyst is filtered off and the filtrate is concentrated under vacuum. 12 g of the expected product are obtained.

Preparation 8.3

N-[4-(3,4-Difluorophenyl)piperid-4-yl]acetamide formate

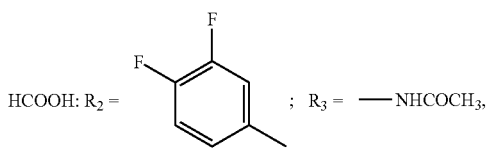

(III)

A) 1-Benzyl-4-(3,4-difluorophenyl)piperid-4-ol

To a suspension of 7.55 g of magnesium in 50 ml of THF is added dropwise a solution of 50 g of 1-bromo-3,4-difluorobenzene in 100 ml of THF so as to reach and then maintain reflux, and the mixture is left at reflux for 2 hours with stirring. After cooling to rt, a solution of 49 g of 1-benzyl-4-piperidinone in 100 ml of THF is added dropwise and the mixture is then stirred at RT overnight. The reaction mixture is poured onto saturated $NH_4Cl$ solution and extracted with ether, the organic phase is dried over $Na_2SO_4$ and the solvent is evaporated under vacuum. 38.3 g of the expected product are obtained after crystallization from cyclohexane.

B) N-[1-Benzyl-4-(3,4-difluorophenyl)piperid-4-yl]acetamide

To a solution of 37 g of the compound obtained in the preceding step in 140 ml of acetonitrile is added dropwise, at a temperature below 30° C., 120 ml of 95% $H_2SO_4$ solution, and the mixture is then stirred at rt overnight. The reaction mixture is poured onto ice, basified by addition of concentrated NaOH solution and extracted with DCM, the organic phase is washed with water, with saturated NaCl solution and dried over $Na_2SO_4$, and the solvent is evaporated off under vacuum. 38.6 g of the expected product are obtained after drying.

C) N-[4-(3,4-Difluorophenyl)piperid-4-yl]acetamide formate

A mixture of 5 g of the compound obtained in the preceding step, 4.65 g of ammonium formate and 0.93 g of 10% palladium-on-charcoal in 100 ml of EtOH is stirred for 4 hours at rt. The catalyst is filtered off and the filtrate is concentrated under vacuum. 4.3 g of the expected product are obtained.

Preparation 8.4

N-[4-(4-Methylphenyl)piperid-4-yl]acetamide formate

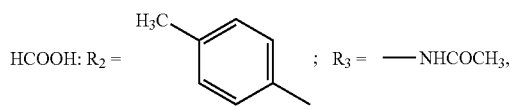

(III)

A) 1-Benzyl-4-(4-methylphenyl)piperid-4-ol

This compound is prepared according to procedure described in step A) of Preparation 8.3, starting with 2.6 g of magnesium in 15 ml of THF, 15 g of 1-bromo-4-methylbenzene in 100 ml of THF and 16.6 g of 1-benzyl-4-piperidinone in 100 ml of THF. 22.9 g of the expected product are obtained.

B) N-[1-Benzyl-4-(4-methylphenyl)piperid-4-yl]acetamide

To a solution of 5.4 g of the compound obtained in the preceding step in 30 ml of acetonitrile is added dropwise, at a temperature below 30° C., 19 ml of 95% $H_2SO_4$ solution, and the mixture is then stirred at rt overnight. The reaction mixture is poured onto ice and basified by addition of concentrated NaOH solution, and the precipitate formed is filtered off by suction. 4.51 g of the expected product are obtained.

C) N-[4-(4-Methylphenyl)piperid-4-yl]acetamide formate

A mixture of 3.5 g of the compound obtained in the preceding step and 2 g of ammonium formate in 80 ml of MeOH is cooled on an ice bath, 0.06 g of 10% palladium-on-charcoal is added and the mixture is stirred overnight while allowing the temperature to rise to rt. The catalyst is filtered off and the filtrate is concentrated under vacuum. 1.63 g of the expected product are obtained after drying.

Preparation 8.5

N-[4-(4-Methoxyphenyl)piperid-4-yl]acetamide formate

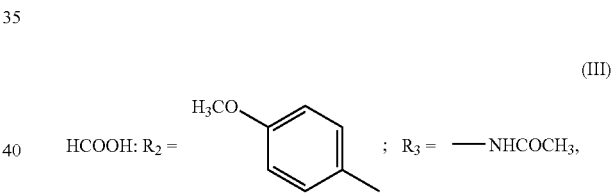

(III)

A) 1-Benzyl-4-(4-methoxyphenyl)piperid-4-ol

A solution of 44.8 g of 1-bromo-4-methoxybenzene in 700 ml of THF is cooled to −78° C., 168 ml of a 1.6M solution of n-butyllithium in hexane are added dropwise and the mixture is then stirred at −78° C. for 30 minutes. The solution of 45.3 g of 1-benzyl-4-piperidinone in 100 ml of THF is then added dropwise and the mixture is stirred at −78° C. for 2 hours. The reaction mixture is poured into 400 ml of saturated $NH_4Cl$ solution and extracted with ether, the organic phase is washed with water, with saturated NaCl solution and dried over $MgSO_4$, and the solvent is evaporated off under vacuum. 48.6 g of the expected product are obtained after crystallization from hexane.

B) N-[1-Benzyl-4-(4-methoxyphenyl)piperid-4-yl]acetamide

To a solution of 48.6 g of the compound obtained in the preceding step in 189 ml of acetonitrile is added dropwise, at a temperature below 27° C., 160 ml of 95% $H_2SO_4$ solution, and the mixture is then stirred for 2 hours and left overnight while cold. The reaction mixture is poured onto ice and basified by addition of 30% NaOH solution, and the precipitate formed is filtered off by suction and washed with water. 49.4 g of the expected product are obtained, and are used without further purification.

C) N-[4-(4-Methoxyphenyl)piperid-4-yl]acetamide formate

A mixture of 2.58 g of the compound obtained in the preceding step, 2.88 g of ammonium formate and 1.7 g of 10% palladium-on-charcoal in 60 ml of EtOH is stirred overnight at rt. The catalyst is filtered off and the filtrate is concentrated under vacuum. 0.7 g of the expected product is obtained.

Preparation 8.6

N-[4-[4-(Trifluoromethoxy)phenyl]piperid-4-yl]acetamide formate

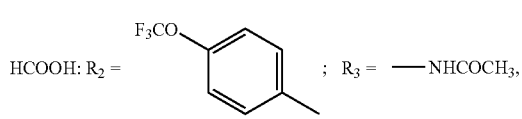

(III)

A) 1-Benzyl-4-[4-(trifluoromethoxy)phenyl]piperid-4-ol

This compound is prepared according to the procedure described in step A of Preparation 8.5, starting with 20 g of 1-bromo-4-(trifluoromethoxy)benzene in 300 ml of THF, 89.3 ml of a 1.6M solution of n-butyllithium in hexane and 24.1 ml of 1-benzyl-4-piperidinone in 50 ml of THF. 18.5 g of the expected product are obtained.

B) N-[1-Benzyl-4-[4-(trifluoromethoxy)phenyl]piperid-4-yl]acetamide

To a mixture of 18.43 g of the compound obtained in the preceding step in 61 ml of acetonitrile is added dropwise, at 25° C., 120 ml of 95% H$_2$SO$_4$ solution, and the mixture is then stirred for 3 hours. The reaction mixture is poured onto ice, basified by addition of concentrated NaOH solution and extracted with EtOAc, the organic phase is washed with water and dried over Na$_2$SO$_4$, and the solvent is evaporated off under vacuum. The residue is taken up in ether and the precipitate formed is filtered off by suction. 9.5 g of the expected product are obtained.

C) N-[4-[4-(Trifluoromethoxy)phenyl]piperid-4-yl]acetamide formate

A mixture of 2.75 g of the compound obtained in the preceding step, 1.97 g of ammonium formate and 1.2 g of 10% palladium-on-charcoal in 50 ml of EtOH is stirred overnight at rt. The catalyst is filtered off and the filtrate is concentrated under vacuum. 2 g of the expected product are obtained.

Preparation 8.7

1-[4-(3-Fluorophenyl)piperid-4-yl]pyrrolidin-2-one (III):

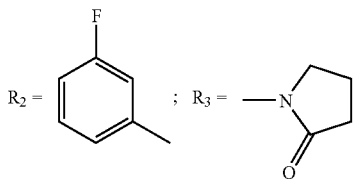

A) 1-Benzyl-4-(3-fluorophenyl)piperid-4-amine

A mixture of 42.5 g of the compound obtained in step B of Preparation 8.2 and 250 ml of 2N HCl solution is refluxed for 48 hours. 100 ml of 4N HCl solution are added and refluxing is continued for 72 hours. After cooling to RT, the reaction mixture is neutralized by addition of concentrated NaOH solution and extracted with EtOAc, the organic phase is washed with water and dried over Na$_2$SO$_4$, and the solvent is evaporated off under vacuum. 37 g of the expected product are obtained.

B) N-[1-Benzyl-4-(3-fluorophenyl)piperid-4-yl]-4-chlorobutanamide

A mixture of 2.7 g of the compound obtained in the preceding step and 1.32 ml of triethylamine in 100 ml of acetonitrile is stirred at RT for 30 minutes, 1.34 g of 4-chlorobutyryl chloride are then added dropwise and the mixture is stirred for 2 hours at rt. The reaction mixture is concentrated under vacuum, the residue is taken up in water and extracted with EtOAc, the organic phase is dried over MgSO$_4$ and the solvent is evaporated off under vacuum. 3 g of the expected product are obtained.

C) 1-[1-Benzyl-4-(3-fluorophenyl)piperid-4-yl]pyrroldin-2-one

A mixture of 3 g of the compound obtained in the preceding step and 0.617 g of 60% sodium hydride in oil in 60 ml of DMF is stirred for 2 hours at rt. Water is added to the reaction mixture, the resulting mixture is extracted with EtOAc, the organic phase is dried over Na$_2$SO$_4$ and the solvent is evaporated off under vacuum. 2.65 g of the expected product are obtained.

D) 1-[4-(3-Fluorophenyl)piperid-4-yl]pyrrolidin-2-one

A mixture of 2.65 g of the compound obtained in the preceding step, 1.43 g of ammonium formate and 1.2 g of 10% palladium-on-charcoal in 50 ml of EtOH is stirred overnight at rt. The catalyst is filtered off and the filtrate is concentrated under vacuum. The residue is taken up in 10% Na$_2$CO$_3$ solution and extracted with EtOAc, the organic phase is dried over Na$_2$SO$_4$ and the solvent is evaporated off under vacuum. 1.6 g of the expected product are obtained after crystallization from ether.

Preparation 8.8

1-[4-(3,4-Difluorophenyl)piperid-4-yl]pyrrolidin-2-one (III):

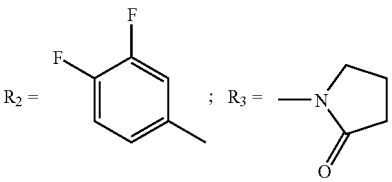

A) 1-Benzyl-4-(3,4-difluorophenyl)piperid-4-amine

A mixture of 14.5 g of the compound obtained in step B) of Preparation 8.3 and 100 ml of 8% HCl solution is refluxed for 48 hours. The reaction mixture is concentrated under vacuum, the residue is taken up in ether and the precipitate formed is filtered off by suction. The precipitate is taken up in 10% Na$_2$CO$_3$ solution and extracted with DCM, the organic phase is dried over Na$_2$SO$_4$ and the solvent is evaporated off under vacuum. 10.75 g of the expected product are obtained.

B) N-[1-Benzyl-4-(3,4-difluorophenyl)piperid-4-yl]-4-chlorobutanamide

A mixture of 3.11 g of the compound obtained in the preceding step and 1.43 ml of triethylamine in 50 ml of acetonitrile is stirred at rt for 30 minutes, 1.16 g of 4-chlorobutyryl chloride are then added dropwise and the mixture is stirred at rt for 5 hours. The reaction mixture is concentrated under vacuum, the residue is extracted with EtOAc, the organic phase is washed with water and dried over Na$_2$SO$_4$, and the solvent is evaporated off under vacuum. 3.73 g of the expected product are obtained.

C) 1-[1-Benzyl-4-(3,4-difluorophenyl)piperid-4-yl]pyrrolidin-2-one

A mixture of 3.73 g of the compound obtained in the preceding step and 0.73 g of 60% sodium hydride in oil in 60 ml of DMF is stirred at rt for 3 hours. Water is added to the reaction medium, the resulting mixture is extracted with EtOAc, the organic phase is dried over Na$_2$SO$_4$ and the solvent is evaporated off under vacuum. 3.7 g of the expected product are obtained in the form of an orange oil.

D) 1-[4-(3,4-Difluoropyhenyl)piperid-4-yl]pyrrolidin-2-one

A mixture of 3.7 g of the compound obtained in the preceding step, 1.9 g of ammonium formate and 1.4 g of 10% palladium-on-charcoal in 60 ml of MeOH is stirred at rt for 4 hours. The catalyst is filtered off, the filtrate is concentrated under vacuum, the residue is taken up in ether and the precipitate formed is filtered off by suction. 2.5 g of the expected product are obtained.

Preparation 8.9

1-[4-(4-Methylphenyl)piperid-4-yl]pyrrolidin-2-one (III):

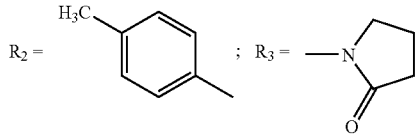

A) N-[1-Benzyl-4-(4-methylphenyl)piperid-4-yl]-4-chlorobutanamide hydrochloride A mixture of 20 g of the compound obtained in step A of Preparation 8.4 and 120.7 ml of 4-chlorobutyronitrile is cooled to 0° C., 50.5 ml of 95% H$_2$SO$_4$ solution are added dropwise and the mixture is stirred at 0-5° C. for 2 hours. The reaction mixture is poured into water, basified to pH 14 by addition of concentrated NaOH solution and extracted with DCM, the organic phase is washed with water and dried over MgSO$_4$, and the solvent is partially concentrated. The insoluble material is filtered off, the filtrate is acidified to pH 1 by addition of 2N hydrochloric ether solution, the mixture is left stirring and the precipitate formed is filtered off by suction. 9.8 g of the expected product are obtained after drying under vacuum.

B) 1-[1-Benzyl-4-(4-methylphenyl)piperid-4-yl]pyrrolidin-2-one

To a solution of 1.9 g of the compound obtained in the preceding step (free base) in 60 ml of DMF is added, at rt, 0.396 g of 60% sodium hydride in oil, and the mixture is stirred at rt overnight. Water is added to the reaction mixture, the resulting mixture is extracted with EtOAc, the organic phase is dried over Na$_2$SO$_4$ and the solvent is evaporated off under vacuum. 1.7 g of the expected product are obtained.

C) 1-[4-(4-Methylphenyl)piperid-4-yl]pyrrolidin-2-one

A mixture of 1.7 g of the compound obtained in the preceding step, 0.934 g of ammonium formate and 0.026 g of 10% palladium-on-charcoal in 100 ml of MeOH is stirred at rt for 3 hours. The catalyst is filtered off and the filtrate is concentrated under vacuum. The residue is taken up in acetone and the precipitate formed is filtered off by suction and washed with acetone. 1.232 g of the expected product are obtained.

Preparation 8.10

1-[4-(4-Methylphenyl)piperid-4-yl]piperidin-2-one (III):

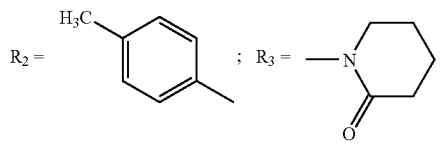

A) N-[1-Benzyl-4-(4-methylphenyl)piperid-4-yl]-5-chloropentanamide hydrochloride A mixture of 6.8 g of the compound obtained in step A of Preparation 8.4 and 50.3 g of 5-chloro-n-valeronitrile is cooled to 0° C., 17.16 ml of 95% $H_2SO_4$ solution are added quickly and the mixture is stirred at 0-5° C. for 4 hours. The reaction mixture is poured into water, basified to pH 14 by addition of concentrated NaOH solution and extracted with DCM, the organic phase is washed with water and dried over $MgSO_4$, and the solvent is evaporated off under vacuum. The residue is taken up in 2N hydrochloric ether solution and left stirring, and the precipitate formed is filtered off by suction. 2 g of the expected product are obtained.

B) 1-[1-Benzyl-4-(4-methylphenyl)piperid-4-yl]piperidin-2-one

To a solution of 1 g of the compound obtained in the preceding step (free base) in 30 ml of DMF is added, at rt, 0.2 g of 60% sodium hydride in oil, and the mixture is stirred overnight at rt. Water is added to the reaction mixture, the resulting mixture is extracted with DCM, the organic phase is washed with water and dried over $Na_2SO_4$, and the solvent is evaporated off under vacuum. The residue is taken up in iso ether and the precipitate formed is filtered off by suction. 0.15 g of the expected product is obtained.

C) 1-[4-(4-Methylphenyl)piperid-4-yl]piperidin-2-one

A mixture of 2 g of the compound obtained in the preceding step, 1.04 g of ammonium formate and 0.29 g of 10% palladium-on-charcoal in 50 ml of MeOH is stirred overnight at rt. The catalyst is filtered off and the filtrate is concentrated under vacuum. 0.7 g of the expected product is obtained.

Preparation 8.11

1-[4-(3-Methylphenyl)piperid-4-yl]pyrrolidin-2-one (III):

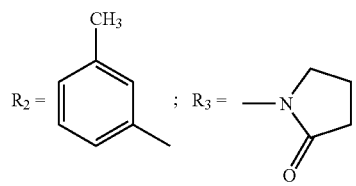

A) 1-Benzyl-4-(3-methylphenyl)piperid-4-ol

This compound is prepared according to the procedure described in step A of Preparation 8.3, starting with 3.4 g of magnesium in 15 ml of THF, a solution of 20 g of 1-bromo-3-methylbenzene in 100 ml of THF and a solution of 22.13 g of 1-benzyl-4-piperidone in 100 ml of THF. 26.54 g of the expected product are obtained.

B) N-[1-benzyl-4-(3-methylphenyl)piperid-4-yl]-4-chlorobutanamide hydrochloride

This compound is prepared according to the procedure described in step A of Preparation 8.9, starting with 24 g of the compound obtained in the preceding step, 14.5 ml of 4-chlorobutyronitrile and 60.6 ml of 95% $H_2SO_4$ solution. 8.3 g of the expected product are obtained.

C) 1-[1-Benzyl-4-(3-methylphenyl)piperid-4-yl]pyrrolidin-2-one

To a solution of 7 g of the compound obtained in the preceding step (free base) in 150 ml of DMF is added, at rt, 1.56 g of 60% sodium hydride in oil, and the mixture is stirred at rt overnight. The reaction mixture is extracted with DCM, the organic phase is washed with water and dried over $Na_2SO_4$, and the solvent is evaporated under vacuum. 6.7 g of the expected product are obtained.

D) 1-[4-(3-Methylphenyl)piperid-4-yl]pyrrolidin-2-one

A mixture of 6.5 g of the compound obtained in the preceding step, 3.53 g of ammonium formate and 0.1 g of 10% palladium-on-charcoal in 150 ml of MeOH is stirred overnight at rt. The catalyst is filtered off, the filtrate is concentrated under vacuum, the residue is taken up in acetone and the precipitate formed is filtered off by suction. 3.5 g of the expected product are obtained.

Preparation 8.12

3-(4-Phenylpiperid-4-yl)-1,3-oxazolidin-2-one (III):

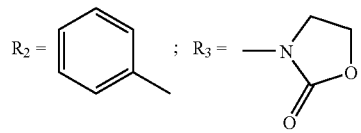

A) 1-[(Benzyloxy)carbonyl]-4-phenylpiperidine-4-carboxylic acid

A mixture of 151 g of 4-phenylpiperidine-4-carboxylic acid p-toluenesulfonate and 213 g of aqueous 30% NaOH solution in 500 ml of water is cooled to 5° C. A solution of 68.2 g of benzyl chloroformate in 150 ml of acetone is added dropwise and the mixture is stirred for 6 days while allowing the temperature to return to rt. 150 ml of acetone are added and the reaction mixture is poured onto a mixture of 200 g of concentrated HCl solution, 300 ml of water and 300 ml of acetone precooled on an ice bath. The precipitate formed is filtered off by suction and washed with water and then with ether. 89.7 g of the expected product are obtained.

B) Benzyl 4-(chlorocarbonyl)-4-phenylpiperidine-1-carboxylate

A mixture of 50.89 g of the compound obtained in the preceding step and 71.4 g of thionyl chloride in 400 ml of 1,2-dichloroethane is refluxed until the evolution of gas has ceased. The reaction mixture is concentrated under vacuum, the residue is taken up in acetone and the solvent is evaporated off under vacuum. 55.3 g of the expected product are obtained in the form of a green oil.

C) Benzyl 4-isocyanato-4-phenylpiperidine-1-carboxylate

A solution of 55.3 g of the compound obtained in the preceding step in 200 ml of acetone is cooled to 5° C., a solution of 19.5 g of sodium azide in 60 ml of water is added dropwise, and the mixture is stirred for 2 hours while allowing the temperature to rise to rt. The reaction mixture is concentrated under vacuum, the residue is taken up in 5% $NaHCO_3$ solution and extracted with toluene, the organic phase is washed with water, with saturated NaCl solution and dried over $Na_2SO_4$, and two thirds of the solvent are concentrated under vacuum. The rest of the toluene solution is refluxed for 1 hour and then concentrated under vacuum. 54 g of the expected product are obtained in the form of an orange oil that crystallizes.

D) Benzyl 4-[[(2-chloroethoxy)carbonyl]amino]-4-phenylpiperidine-1-carboxylate

A mixture of 3.36 g of the compound obtained in the preceding step and 8.04 g of 2-chloroethanol in 50 ml of 1,2-dichloroethane is refluxed for 5 hours and then stirred overnight at rt. The reaction mixture is concentrated under vacuum, the residue is taken up in pentane and triturated, and the precipitate formed is filtered off by suction and washed with pentane. 3.7 g of the expected product are obtained.

E) Benzyl 4-(2-oxo-1,3-oxazolidin-3-yl)-4-phenylpiperidine-1-carboxylate

A mixture of 3.7 g of the compound obtained in the preceding step and 0.7 g of 60% sodium hydride in oil in 50 ml of DMF is stirred overnight at rt. The reaction mixture is concentrated under vacuum, the residue is taken up in a pH 2 buffer solution and extracted with EtOAc, the organic phase is washed with water and dried over $Na_2SO_4$, and the solvent is evaporated off under vacuum. The residue is taken up in an iso ether/pentane mixture and triturated, and the precipitate formed is filtered off by suction and washed with iso ether. 2.7 g of the expected product are obtained.

F) 3-(4-Phenylpiperid-4-yl)-1,3-oxazolidin-2-one

A mixture of 2.7 g of the compound obtained in the preceding step, 1.34 g of ammonium formate and 0.45 g of 10% palladium-on-charcoal in 50 ml of EtOH is heated at 50° C. for 1 hour. The catalyst is filtered off and the filtrate is concentrated under vacuum. 1.7 g of the expected product are obtained.

Preparation 8.13

3-[4-(3-Fluorophenyl)piperid-4-yl]-1,3-oxazolidin-2-one (III):

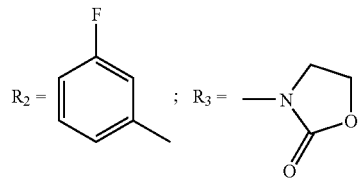

A) 2-Chloroethyl [1-benzyl-4-(3-fluorophenyl)piperid-4-yl]carbamate

To a solution of 9 g of the compound obtained in step A of Preparation 8.7 and 3.84 g of triethylamine in 100 ml of 1,2-dichloroethane is added, at rt, 4.52 g of 2-chloroethyl chloroformate, and the mixture is stirred for 1 hour at rt. The reaction mixture is concentrated under vacuum, the residue is extracted with EtOAc, the organic phase is washed with water and dried over $Na_2SO_4$, and the solvent is evaporated off under vacuum. The residue is chromatographed on silica H gel, eluting with a DCM/MeOH mixture (100/1; v/v). 3.2 g of the expected product are obtained.

B) 3-[1-Benzyl-4-(3-fluorophenyl)piperid-4-yl]-1,3-oxazolidin-2-one

To a solution of 3.2 g of the compound obtained in the preceding step in 30 ml of DMF is added, at rt, 0.65 g of 60% sodium hydride in oil, and the mixture is stirred at rt for 1 hour and then heated at 30° C. for 1 hour. The reaction mixture is concentrated under vacuum, the residue is taken up in water and the precipitate formed is filtered off by suction and washed with water. 2.4 g of the expected product are obtained after drying under vacuum.

C) 3-[4-(3-Fluorophenyl)piperid-4-yl]-1,3-oxazolidin-2-one

A mixture of 2.4 g of the compound obtained in the preceding step, 1.28 g of ammonium formate and 0.43 g of 10% palladium-on-charcoal in 150 ml of EtOH is heated at 50-60° C. for 3 hours. After cooling to rt, the catalyst is filtered off and the filtrate is concentrated under vacuum. 1.2 g of the expected product are obtained.

Preparation 8.14

3-[4-(4-Fluorophenyl)piperid-4-yl]-1,3-oxazolidin-2-one (III):

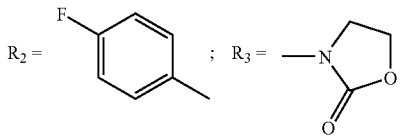

A) tert-Butyl bis(2-chloroethyl)carbamate

To a mixture of 75 g of bis(2-chloroethyl)-amine hydrochloride and 91.7 g of di-tert-butyl dicarbonate in 1000 ml of DCM is added dropwise, at rt, 61.2 ml of triethylamine, and the mixture is stirred overnight at rt. The reaction mixture is concentrated under vacuum, the residue is extracted with ether, the organic phase is washed with water, with a pH 2 buffer solution, with 5% NaHCO$_3$ solution and with saturated NaCl solution and dried over Na$_2$SO$_4$, and the solvent is evaporated off under vacuum. 101 g of the expected product are obtained in the form of an oil, which is used without further purification.

B) tert-Butyl 4-cyano-4-(4-fluorophenyl)piperidine-1-carboxylate

To a mixture of 33.3 g of 60% sodium hydride in oil in 200 ml of DMSO and 100 ml of THF is added dropwise, at rt, a solution of 50 ml of 4-fluorophenylacetonitrile and 101 g of the compound obtained in the preceding step in 200 ml of THF, and the mixture is stirred for 2 hours at rt and then refluxed for 1 hour and stirred at rt overnight. The reaction mixture is poured into saturated NH$_4$Cl solution, the THF is concentrated under vacuum, the aqueous phase is diluted with water and extracted with ether, the organic phase is dried over Na$_2$SO$_4$ and the solvent is evaporated off under vacuum. The orange oil obtained is taken up in a minimum amount of ether and the crystalline product formed is filtered off by suction. 87.6 g of the expected product are obtained.

C) 4-(4-Fluorophenyl)piperidine-4-carbonitrile hydrochloride

A mixture of 87.6 g of the compound obtained in the preceding step and 33 ml of concentrated HCl solution in 330 ml of MeOH is refluxed for 4 hours. The reaction mixture is concentrated under vacuum, the residue is taken up in acetone and the crystalline product formed is filtered off by suction. 54.71 g of the expected product are obtained.

D) 4-(4-Fluorophenyl)piperidine-4-carboxylic acid

A mixture of 54.71 g of the compound obtained in the preceding step and 57 g of potassium hydroxide in 360 ml of diethylene glycol is refluxed for 7 hours and then stirred overnight at rt. The volume of the reaction mixture is made up to 900 ml by addition of ice, the mixture is neutralized to pH 7 by addition of concentrated HCl solution, and the resulting mixture is stirred for 2 hours. The precipitate formed is filtered off by suction and washed with acetone. 31.56 g of the expected product are obtained.

E) 1-[(Benzyloxy)carbonyl]-4-(4-fluorophenyl)-piperidine-4-carboxylic acid

To a mixture of 31.56 g of the compound obtained in the preceding step and 56.4 g of 30% NaOH solution in 320 ml of water is added 50 ml of acetone, the resulting mixture is cooled on an ice bath, 20.12 ml of benzyl chloroformate are added dropwise and this mixture is stirred overnight at rt. The reaction mixture is washed with ether, the aqueous phase is acidified to pH 1 by addition of concentrated HCl solution and extracted with EtOAc, the organic phase is washed with water, with saturated NaCl solution and dried over Na$_2$SO$_4$, and the solvent is evaporated off under vacuum. The residue is chromatographed on silica H gel, eluting with DCM and then with a DCM/MeOH mixture (100/2; v/v). 30.39 g of the expected product are obtained.

F) Benzyl 4-(chlorocarbonyl)-4-(4-fluorophenyl)-piperidine-1-carboxylate

To a solution of 30.39 g of the compound obtained in the preceding step in 200 ml of 1,2-dichloroethane is added 25 ml of thionyl chloride, and the mixture is then refluxed for 4 hours. The reaction mixture is concentrated under vacuum, the residue is taken up in DCM and the solvent is evaporated off under vacuum. 31.8 g of the expected product are obtained.

G) Benzyl 4-(4-fluorophenyl)-4-isocyanatopiperidine-1-carboxylate

A solution of 31.8 g of the compound obtained in the preceding step in 200 ml of acetone is cooled on an ice bath, a solution of 11.1 g of sodium azide in 15 ml of water is added dropwise and the mixture is stirred for 1 hour at rt. The reaction mixture is concentrated under vacuum, the residue is extracted with toluene, the organic phase is washed with 5% NaHCO$_3$ solution, with saturated NaCl solution and dried over Na$_2$SO$_4$. The resulting toluene solution is refluxed for 1 hour and then concentrated under vacuum. The residue is taken up in pentane and the precipitate formed is filtered off by suction. 26 g of the expected product are obtained.

H) Benzyl 4-[[(2-chloroethoxy)carbonyl]amino]-4-(4-fluorophenyl)piperidine-1-carboxylate A mixture of 1.77 g of the compound obtained in the preceding step and 0.4 g of 2-chloroethanol in 50 ml of 1,2-dichloroethane is refluxed for 4 hours and then stirred overnight at rt and concentrated under vacuum. 2.1 g of the expected product are obtained.

I) Benzyl 4-(4-fluorophenyl)-4-(2-oxo-1,3-oxazolidin-3-yl)piperidine-1-carboxylate A mixture of 2.1 g of the compound obtained in the preceding step and 0.386 g of 60% sodium hydride in oil in 20 ml of DMF is stirred for 2 hours at rt. The reaction mixture is concentrated under vacuum, the residue is taken up in a pH 2 buffer solution and extracted with EtOAc, the organic phase is washed with water and dried over Na$_2$SO$_4$, and the solvent is evaporated off under vacuum. The residue is taken up in pentane and triturated, and the precipitate formed is filtered off by suction. 1.5 g of the expected product are obtained.

J) 3-[4-(4-Fluorophenyl)piperid-4-yl]-1,3-oxazolidin-2-one

A mixture of 1.5 g of the compound obtained in the preceding step, 0.7 g of ammonium formate and 0.2 g of 10% palladium-on-charcoal in 20 ml of EtOH is stirred for 1 hour at 40° C. The catalyst is filtered off and the filtrate is concentrated under vacuum. 0.9 g of the expected product is obtained.

Preparation 8.15

3-[4-(3,4-Dimethylphenyl)piperid-4-yl]-1,3-oxazolidin-2-one (III):

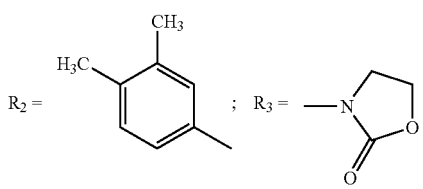

A) Benzyl[bis(2-chloroethyl)]amine

A mixture of 150 g of bis(2-chloroethyl)amine hydrochloride and 144 g of benzyl bromide in 1000 ml of DMF is cooled on an ice bath, 120 ml of triethylamine are added dropwise and the mixture is then stirred for 5 hours at rt. The reaction mixture is concentrated under vacuum, the residue is taken up in water and extracted with ether, the organic phase is dried over $Na_2SO_4$ and the solvent is evaporated off under vacuum. 110 g of the expected product are obtained.

B) 1-Benzyl-4-(3,4-dimethylphenyl)piperidine-4-carbonitrile

To a suspension of 5.78 g of 60% sodium hydride in oil in 20 ml of THF and 10 ml of DMSO is added dropwise a solution of 10 g of 3,4-dimethyl-phenylacetonitrile in 50 ml of DMSO, and the mixture is then stirred for 30 minutes at rt. A solution of 14 g of the compound obtained in the preceding step in 50 ml of DMSO is then added dropwise and the mixture is stirred overnight at rt. The reaction mixture is concentrated under vacuum, the residue is taken up in water and extracted with ether, the organic phase is dried over $Na_2SO_4$ and the solvent is evaporated off under vacuum. The residue is taken up in a 2N hydrochloric ether solution and the precipitate formed is filtered off by suction and washed with pentane. 18 g of the expected product are obtained.
m.p.=265-267° C.

C) 1-Benzyl-4-(3,4-dimethylphenyl)piperidine-4-carboxylic acid

A mixture of 15 g of the compound obtained in the preceding step and 11.06 g of KOH pellets in 100 ml of ethylene glycol is refluxed for 24 hours. After cooling to rt, water is added to the reaction mixture, the aqueous phase is washed with ether and neutralized to pH 7 by addition of concentrated HCl solution, and the precipitate formed is filtered off by suction. 10.6 g of the expected product are obtained.

D) 1-Benzyl-4-(3,4-dimethylphenyl)piperidine-4-carbonyl chloride hydrochloride A mixture of 10.6 g of the compound obtained in the preceding step and 8.76 ml of thionyl chloride in 100 ml of 1,2-dichloroethane is refluxed for 6 hours and then stirred overnight at rt. The reaction mixture is concentrated under vacuum, the residue is taken up in ether and the precipitate formed is filtered off by suction and washed with ether and with pentane. 9 g of the expected product are obtained, and are used without further purification.

E) 1-Benzyl-4-(3,4-dimethylphenyl)-4-isocyanatopiperidine

A solution of 9 g of the compound obtained in the preceding step and 5.16 ml of triethylamine in 200 ml of acetone is cooled to 0° C., a solution of 3.1 g of sodium azide in 15 ml of water is added dropwise and the mixture is stirred while allowing the temperature to rise to rt. The reaction mixture is concentrated under vacuum, the residue is extracted with toluene, the organic phase is washed with water and dried over $Na_2SO_4$, and the toluene phase is refluxed for 3 hours. The reaction mixture is concentrated under vacuum to give 4 g of the expected product, which is used without further purification.

F) 2-Chloroethyl [1-benzyl-4-(3,4-dimethylphenyl)-piperid-4-yl]carbamate

A mixture of 4 g of the compound obtained in the preceding step and 10.05 g of 2-chloroethanol in 50 ml of 1,2-dichloroethane is refluxed for 4 hours. The reaction mixture is concentrated under vacuum and the residue is chromatographed on silica gel, eluting with a DCM/MeOH mixture (100/5; v/v). 2 g of the expected product are obtained, and are used without further purification.

G) 3-[1-Benzyl-4-(3,4-dimethylphenyl)piperid-4-yl]-1,3-oxazolidin-2-one

A mixture of 2 g of the compound obtained in the preceding step and 0.4 g of 60% sodium hydride in oil in 20 ml of DMF is stirred for 2 hours at rt. The reaction mixture is concentrated under vacuum, the residue is taken up in water and extracted with EtOAc, the organic phase is washed with water and dried over $MgSO_4$, and the solvent is evaporated off under vacuum. 1.4 g of the expected product are obtained.

H) 3-[4-(3,4-Dimethylphenyl)piperid-4-yl]-1,3-oxazolidin-2-one

A mixture of 1.4 g of the compound obtained in the preceding step, 0.73 g of ammonium formate and 0.41 g of 10% palladium-on-charcoal in 30 ml of EtOH is stirred at 30° C. for 2 hours. The catalyst is filtered off and the filtrate is concentrated under vacuum. 1 g of the expected product is obtained.

Preparation 8.16

3-(4-Phenylpiperid-4-yl)-1,3-oxazinan-2-one formate

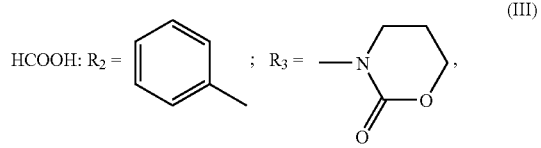

A) Benzyl 4-[[(3-chloropropoxy)carbonyl]amino]-4-phenylpiperidine-1-carboxylate A mixture of 4 g of the compound obtained in step C of Preparation 8.12 and 5 ml of 3-chloro-1-propanol in 100 ml of 1,2-dichloroethane is refluxed for 4 hours. A further 5 ml of 3-chloro-1-propanol are added and refluxing is continued for 1 hour. A further 5 ml of 3-chloro-1-propanol are added and the mixture is stirred overnight at rt. The reaction mixture is concentrated under vacuum to give 4.14 g of the expected product.

B) Benzyl 4-(2-oxo-1,3-oxazinan-3-yl)-4-phenylpiperidine-1-carboxylate

A mixture of 4.14 g of the compound obtained in the preceding step and 0.769 g of 60% sodium hydride in oil in 50 ml of DMF is stirred for 2 hours at rt. The reaction mixture is concentrated under vacuum, the residue is taken up in iso ether and the precipitate formed is filtered off by suction. 3.19 g of the expected product are obtained after drying under vacuum.

C) 3-(4-Phenylpiperid-4-yl)-1,3-oxazinan-2-one formate

A mixture of 3.19 g of the compound obtained in the preceding step, 1.53 g of ammonium formate and 0.43 g of 10% palladium-on-charcoal in 60 ml of EtOH is stirred for 3 hours at rt. The catalyst is filtered off and the filtrate is concentrated under vacuum. 1 g of the expected product is obtained.

Preparation 8.17

3-[4-(4-Fluorophenyl)piperid-4-yl]-1,3-oxazinan-2-one formate

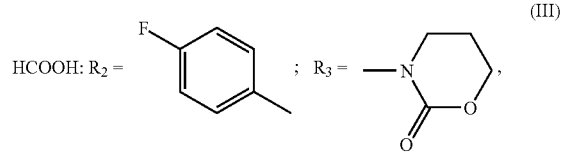

A) Benzyl 4-[[(3-chloropropoxy)carbonyl]amino]-4-(4-fluorophenyl)piperidine-1-carboxylate A mixture of 2 g of the compound obtained in step G of Preparation 8.14 and 8 g of 3-chloro-1-propanol in 20 ml of 1,2-dichloroethane is refluxed for 1 hour. The reaction mixture is concentrated under vacuum, the residue is taken up in pentane and stirred for 1 hour, and the precipitate formed is filtered off by suction. 2.5 g of the expected product are obtained after drying under vacuum.

B) Benzyl 4-(4-fluorophenyl)-4-(2-oxo-1,3-oxazinan-3-yl)piperidine-1-carboxylate A mixture of 2.5 g of the compound obtained in the preceding step and 0.445 g of 60% sodium hydride in oil in 20 ml of DMF is stirred for 1 hour at rt. The reaction mixture is concentrated under vacuum, the residue is taken up in a pH 2 buffer solution and extracted with EtOAc, the organic phase is washed with water and dried over $Na_2SO_4$, and the solvent is evaporated off under vacuum. The residue is taken up in an iso ether/pentane mixture and triturated, and the precipitate formed is filtered off by suction. 1.1 g of the expected product are obtained.

C) 3-[4-(4-Fluorophenyl)piperid-4-yl]-1,3-oxazinan-2-one formate

A mixture of 1.1 g of the compound obtained in the preceding step, 0.5 g of ammonium formate and 0.14 g of 10% palladium-on-charcoal in 20 ml of EtOH is stirred for 1 hour at rt. The catalyst is filtered off and the filtrate is concentrated under vacuum. 0.7 g of the expected product is obtained.

Preparation 8.18

3-[4-(3,4-Difluorophenyl)piperid-4-yl]-1,3-oxazinan-2-one

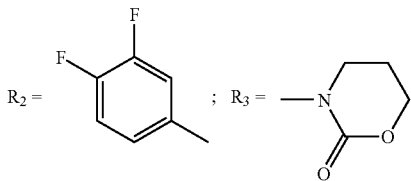

A) 4-(3,4-Difluorophenyl)piperid-4-amine

A mixture of 33 g of the compound obtained in step A of Preparation 8.8 and 18.42 g of ammonium formate in 500 ml of MeOH is cooled on an ice bath, 0.5 g of 10% palladium-on-charcoal is added, the mixture is stirred for 3 hours while allowing the temperature to use to RT, and is then heated at 40° C. for 1 hour. The catalyst is filtered off and the filtrate is concentrated under vacuum. 28 g of the expected product are obtained.

B) Benzyl 4-amino-4-(3,4-difluorophenyl)piperidine-1-carboxylate

To a mixture of 27.5 g of the compound obtained in the preceding step and 57.7 ml of triethylamine in 500 ml of DCM is added dropwise, at rt, 22.1 g of benzyl chloroformate, and the mixture is stirred overnight at rt. The reaction mixture is concentrated under vacuum, the residue is extracted with DCM, the organic phase is washed with water, with saturated NaCl solution and dried over $Na_2SO_4$, and the solvent is evaporated off under vacuum. The residue is chromatographed on silica gel, eluting with DCM/MeOH (95/5; v/v). 11.51 g of the expected product are obtained.

C) Benzyl 4-[[(3-chloropropoxy)carbonyl]amino]-4-(3,4-difluorophenyl)piperidine-1-carboxylate To a mixture of 5 g of the compound obtained in the preceding step and 4.42 ml of triethylamine in 100 ml of DCM is added dropwise, at rt, 2.27 g of 3-chloropropyl chloroformate, and the mixture is stirred overnight at rt. The reaction mixture is concentrated under vacuum, the residue is extracted with DCM, the organic phase is washed with water, with saturated NaCl solution and dried over $Na_2SO_4$, and the solvent is evaporated off under vacuum. The residue is chromatographed on silica H gel, eluting with DCM and then with a DCM/MeOH mixture (100/2; v/v). 1.9 g of the expected product are obtained.

D) Benzyl 4-(3,4-difluorophenyl)-4-(2-oxo-1,3-oxazinan-3-yl)piperidine-1-carboxylate A mixture of 1.9 g of the compound obtained in the preceding step and 0.33 g of 60% sodium hydride in oil in 30 ml of DMF is stirred for 2 hours at rt. The reaction mixture is concentrated under vacuum, the residue is taken up in iso ether and the precipitate formed is filtered off by suction. 1.5 g of the expected product are obtained after drying under vacuum.

E) 3-[4-(3,4-Difluorophenyl)piperid-4-yl]-1,3-oxazinan-2-one

A mixture of 1.5 g of the compound obtained in the preceding step, 0.66 g of ammonium formate and 0.18 g of 10% palladium-on-charcoal in 50 ml of EtOH is stirred overnight at rt. The catalyst is filtered off and the filtrate is concentrated under vacuum. 0.87 g of the expected product is obtained.

Preparation 8.19

4-[(4-phenylpiperid-4-yl)carbonyl]morpholine (III):

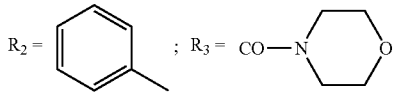

This compound is prepared according to the procedures described in Preparation 1.29 in WO 97/10211.

Preparation 8.20

1,4'-Dipiperidine-4'-carboxamide formate (III):

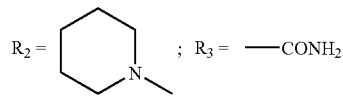

A) Benzyl 1,4'-bipiperidine-4'-carboxamide

This compound is prepared according to the procedure described in step B of Preparation 3.1 in WO 02/094821.

B) 1,4'-Bipiperidine-4'-carboxamide formate

A mixture of 50 g of the compound obtained in the preceding step, 31.4 g of ammonium formate and 12.5 g of 50% palladium-on-charcoal in 200 ml of MeOH is stirred for 4 hours 30 minutes. The catalyst is filtered off and the filtrate is concentrated under vacuum. 22.5 g of the expected product are obtained.

Preparation 8.21

3-[4-(3,4-Difluorophenyl)piperid-4-yl]-1,3-oxazolidin-2-one (III):

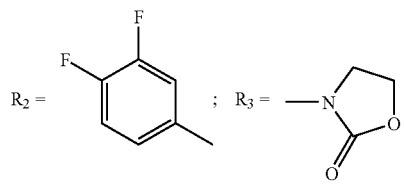

A) Benzyl 4-[[(2-chloroethoxy)carbonyl]amino]-4-(3,4-difluorophenyl)piperidine-1-carboxylate To a solution of 5 g of the compound obtained in step B of Preparation 8.18 and 4.42 ml of triethylamine in 100 ml of DCM is added dropwise, at rt, 2.06 g of 2-chloroethyl chloroformate, and the mixture is stirred overnight at RT. The reaction mixture is concentrated under vacuum, the residue is extracted with DCM, the organic phase is washed with water, with saturated NaCl solution and dried over $Na_2SO_4$, and the solvent is evaporated off under vacuum. The residue is chromatographed on silica H gel, eluting with DCM and then with a DCM/MeOH mixture (97/3; v/v). 1.55 g of the expected product are obtained.

B) Benzyl 4-(3,4-difluorophenyl)-4-(2-oxo-1,3-oxazolidin-3-yl)piperidine-1-carboxylate To a mixture of 1.5 g of the compound obtained in the preceding step in 50 ml of DMF is added 0.16 g of 60% sodium hydride in oil, and the mixture is stirred for 2 hours at rt. The reaction mixture is concentrated under vacuum, the residue is taken up in iso ether and the precipitate formed is filtered off by suction and dried under vacuum. 1.16 g of the expected product are obtained.

C) 3-[4-(3,4-Difluorophenyl)piperid-4-yl]-1,3-oxazolidin-2-one

A mixture of 1.15 g of the compound obtained in the preceding step, 0.52 g of ammonium formate and 0.15 g of 10% palladium-on-charcoal in 60 ml of EtOH is stirred overnight at rt. The catalyst is filtered off and the filtrate is concentrated under vacuum. 0.73 g of the expected product is obtained.

Preparation 8.22

N-[4-[3-Trifluoromethyl)phenyl]piperid-4-yl]acetamide formate (III):

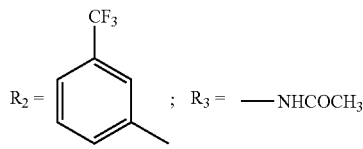

A)
1-Benzyl-4-[3-(trifluoromethyl)phenyl]piperid-4-ol

To a mixture of 24.5 g of 4-hydroxy-4-[3-(trifluoromethyl)phenyl]piperidine (commercial) and 27.6 g of $K_2CO_3$ in 20 ml of DMF is added dropwise, at rt, 17.1 g of benzyl bromide, and the mixture is then heated at 40° C. for 2 hours and stirred overnight at rt. The reaction mixture is concentrated under vacuum, the residue is taken up in water and extracted with EtOAc, the organic phase is washed with water and dried over $Na_2SO_4$, and the solvent is evaporated off under vacuum. 31 g of the expected product are obtained.

B) N-[1-Benzyl-4-[3-(trifluoromethyl)phenyl]piperidin-4-yl]acetamide

To a solution of 31 g of the compound obtained in the preceding step in 107 ml of acetonitrile is added dropwise, at a temperature below 20° C., 88.65 ml of 95% $H_2SO_4$, and the mixture is stirred for 6 hours at rt. The reaction mixture is poured into ice and neutralized by addition of concentrated NaOH solution, and the precipitate formed is filtered off by suction, washed with water and dried. 17.7 g of the expected product are obtained after crystallization from 2-propanol.

C) N-[4-[3-(trifluoromethyl)phenyl]piperid-4-yl]acetamide formate

A mixture of 3 g of the compound obtained in the preceding step, 1.5 g of ammonium formate and 0.4 g of 10% palladium-on-charcoal in 60 ml of MeOH is stirred overnight at rt. The catalyst is filtered off and the filtrate is concentrated under vacuum. 3 g of the expected product are obtained.

Preparation 8.23

4-(2-Pyridyl)piperid-4-ol formate (III):

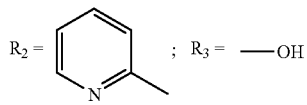

A) 1-Benzyl-4-(pyrid-2-yl)piperid-4-ol

A solution of 22.2 g of 2-bromopyridine in 100 ml of THF is cooled to −70° C., 87.8 ml of n-butyllithium are added dropwise and the mixture is stirred for 30 minutes. A solution of 25.6 g of 1-benzyl-4-piperidinone in 100 ml of THF is then added dropwise at −60° C., and the mixture is stirred overnight while allowing the temperature to rise to rt. The reaction mixture is poured into water and extracted with ether, the organic phase is washed with water and dried over $Na_2SO_4$, and the solvent is evaporated off under vacuum. The residue is chromatographed on silica H gel, eluting with DCM and then with a DCM/MeOH mixture gradient of from (99/1; v/v) to (90/10; v/v). 21.5 g of the expected product are obtained.

B) 4-(2-Pyridyl)piperid-4-ol formate

A mixture of 5 g of the compound obtained in the preceding step, 3.5 g of ammonium formate and 0.1 g of 10% palladium-on-charcoal in 50 ml of MeOH is stirred for 4 hours at rt. The catalyst is filtered off and the filtrate is concentrated under vacuum. 3.4 g of the expected product are obtained.

Preparation 8.24

3-[4-(4-Chlorophenyl)piperid-4-yl]-1,3-oxazolidin-2-one hydrochloride (III):

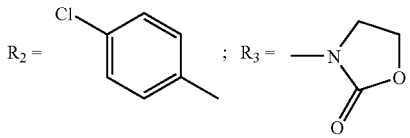

A) 1-Benzyl-4-(4-chlorophenyl)piperidine-4-carbonitrile

To a suspension of 9.8 g of 60% sodium hydride in oil in 140 ml of THF and 60 ml of DMSO is added dropwise, at rt, a solution of 11.3 g of 4-chlorophenylacetonitrile and 20 g of benzyl[bis(2-chloroethyl)]amine hydrochloride in 140 ml of THF and 60 ml of DMSO, and the mixture is then heated at 70-80° C. for 2 hours. After cooling, the reaction mixture is poured onto ice and extracted with ether, the organic phase is washed with water and dried over $Na_2SO_4$, and the solvent is evaporated off under vacuum. The residue is chromatographed on silica gel, eluting with a heptane/EtOAc mixture (90/10; v/v). 19.6 g of the expected compound are obtained.

B) 1-Benzyl-4-(4-chlorophenyl)piperidine-4-carboxylic acid

A mixture of 19.6 g of the compound obtained in the preceding step and 14.15 g of KOH pellets in 150 ml of ethylene glycol is heated at 200° C. for 18 hours. After cooling to rt, the reaction mixture is poured onto ice, the aqueous phase is washed with ether and acidified to pH 6.5 by addition of concentrated HCl solution, and the precipitate formed is filtered off by suction, washed with water and then with acetone, and dried. 19 g of the expected compound are obtained.

C) 1-Benzyl-4-(4-chlorophenyl)piperidine-4-carbonyl chloride hydrochloride

A mixture of 19 g of the compound obtained in the preceding step and 40.5 ml of thionyl chloride is refluxed for 4 hours and then stirred at rt overnight. The reaction mixture is concentrated under vacuum, the residue is taken up in toluene and the solvent is evaporated off under vacuum. 21 g of the expected compound are obtained, and are used without further purification.

D) 1-Benzyl-4-(4-chlorophenyl)-4-isocyanatopiperidine

A suspension of 20.5 g of the compound obtained in the preceding step and 13 ml of triethylamine in 200 ml of acetone is cooled to 0° C., a solution of 9.6 g of sodium azide in 50 ml of water is added dropwise, the mixture is stirred for 30 minutes and then left for 1 hour at rt. The reaction mixture is concentrated under vacuum, the residue is extracted with toluene, the organic phase is washed with water and dried over Na$_2$SO$_4$, and the toluene phase is refluxed for 4 hours. After stirring overnight at rt, the solvent is evaporated off under vacuum to give 10.5 g of the expected compound, which is used without further purification.

E) 2-Chloroethyl [1-benzyl-4-(4-chlorophenyl)piperid-4-yl]carbamate

A mixture of 10.5 g of the compound obtained in the preceding step and 20 ml of 2-chloroethanol is heated at 80° C. for 1 hour and then stirred overnight at rt. The reaction mixture is concentrated under vacuum, the residue is extracted with EtOAc, the organic phase is washed with water and dried over Na$_2$SO$_4$, and the solvent is evaporated off under vacuum. The residue is chromatographed on silica gel, eluting with DCM and then with a DCM/MeOH mixture gradient of from (99/1; v/v) to (90/10; v/v). 8.3 g of the expected compound are obtained.

F) 3-[1-Benzyl-4-(4-chlorophenyl)piperid-4-yl]-1,3-oxazolidin-2-one

To a solution of 8 g of the compound obtained in the preceding step in 45 ml of DMF is added portionwise, at rt, 1.73 g of 60% sodium hydride in oil, and the mixture is then heated at 50° C. for 1 hour. The reaction mixture is concentrated under vacuum, the residue is taken up in water and extracted with EtOAc, the organic phase is washed with water and dried over Na$_2$SO$_4$, and the solvent is evaporated off under vacuum. The residue is taken up in pentane and triturated, and the precipitate formed is filtered off by suction and washed with pentane. 6.2 g of the expected compound are obtained.

G) 3-(4-(4-Chlorophenyl)piperid-4-yl]-1,3-oxazolidin-2-one hydrochloride

A mixture of 6.2 g of the compound obtained in the preceding step and 2.3 g of K$_2$CO$_3$ in 60 ml of DCM is cooled to 0° C., 2.87 g of 1-chloroethyl chloroformate are added dropwise and the mixture is stirred for 1 hour under the cold conditions, and then for 1 hour at rt. The insoluble material is filtered off and the filtrate is concentrated under vacuum. The residue is taken up in 50 ml of MeOH and stirred overnight at rt. This mixture is concentrated under vacuum, the residue is dissolved in a DCM/MeOH mixture and added to an ether/pentane mixture, and the precipitate formed is filtered off by suction and washed with ether. 4.2 g of the expected compound are obtained.

Preparation 8.25

N,N-Dimethyl-1,4'-bipiperidine-4'-carboxamide (III):

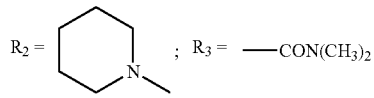

$R_2 = $ 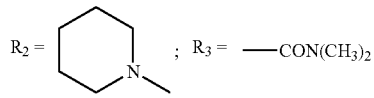 ; $R_3 = $ —CON(CH$_3$)$_2$

This compound is prepared according to the procedures described in Preparation 3.1 in WO 02/094821.

EXAMPLES

Example 1

Compound 1

6-(3,4-Dichlorophenyl)-6-[2-[4-hydroxy-4-[3-(trifluoromethyl)phenyl]piperid-1-yl]ethyl]-4-phenylmorpholin-3-one hydrochloride, dextrorotatory isomer (I)

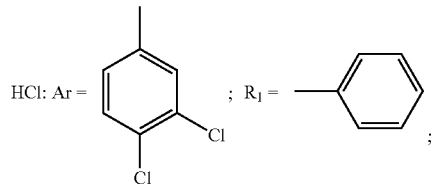

HCl: Ar = ; R$_1$ =

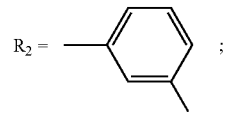 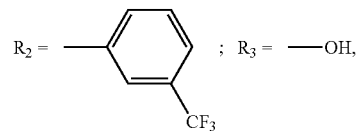

R$_2$ = ; R$_3$ = —OH,

To a solution of 0.5 g of the compound obtained in Preparation 7.1 in 20 ml of DCM is added 0.337 g of 4-hydroxy-4-[3-(trifluoromethyl)phenyl]-piperidine (commercial) followed by addition of 0.61 g of sodium triacetoxyborohydride and 0.0085 g of acetic acid, and the mixture is stirred overnight at rt. The reaction mixture is basified by addition of 10% Na$_2$CO$_3$ solution and extracted with DCM, the organic phase is washed with water and dried over Na$_2$SO$_4$, and the solvent is evaporated off under vacuum. The residue is chromatographed on silica H gel, eluting with DCM and then with a DCM/EtOH mixture gradient up to (98/2; v/v). The product obtained is taken up in 2N hydrochloric ether and concentrated under vacuum, the residue is dissolved in DCM, ether is added and the precipitate formed is filtered off by suction. 0.42 g of the expected product is obtained.

$\alpha_D^{20} = +30°$ ($c=0.25$; MeOH).

Example 2

Compound 3

N-[1-[2-[2-(3,4-Dichlorophenyl)-5-oxo-4-phenyl-morpholin-2-yl]ethyl]-4-(3-fluorophenyl)piperid-4-yl]acetamide hydrochloride, dextrorotatory isomer

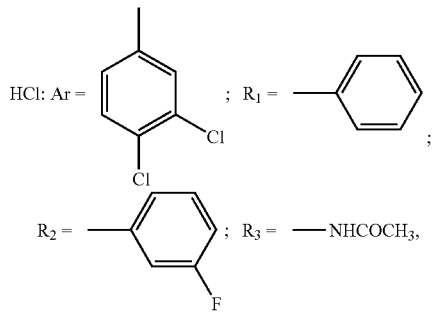

(I)

To a solution of 0.5 g of the compound obtained in Preparation 7.1 in 20 ml of DCM is added 0.387 g of the compound obtained in Preparation 8.2, followed by addition 0.61 g of sodium triacetoxyborohydride and 0.0085 g of acetic acid, and the mixture is stirred overnight at rt. The reaction mixture is basified by addition of 10% $Na_2CO_3$ solution and extracted with DCM, the organic phase is washed with water and dried over $Na_2SO_4$, and the solvent is evaporated off under vacuum. The residue is chromatographed on silica H gel, eluting with DCM and then with a DCM/MeOH mixture gradient up to (97/3; v/v). The product obtained is taken up 2N hydrochloric ether and concentrated under vacuum, the residue is dissolved in DCM, ether is added and the precipitate formed is filtered off by suction. 0.57 g of the expected product is obtained.

$\alpha_D^{20}$=+29.8° (c=0.5; MeOH).

$^1$H NMR: DMSO-$d_6$: δ (ppm): 1.9: s: 3H, 2.3: mt: 2H, 2.4-3.7: m: 10H, 4.0-4.75: m: 4H, 7.0-7.9: m: 12H, 8.2: s: 1H; 11: bs: 1H.

Example 3

Compound 4

N-[1-[2-[2-(3,4-Dichlorophenyl)-5-oxo-4-phenyl-morpholin-2-yl]ethyl]-4-(3-fluorophenyl)piperid-4-yl]acetamide fumarate, dextrorotatory isomer

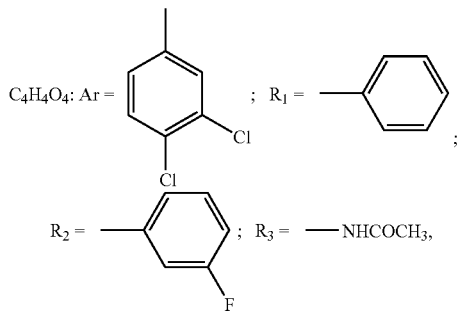

(I)

A solution of 4.5 g of compound 3 in free base form in 72 ml of acetonitrile is heated to reflux, 0.896 g of fumaric acid is added and refluxing is continued for 30 minutes. The reaction mixture is cooled to rt and stirred for 1 hour at rt. The crystalline product formed is filtered off by suction and dried under vacuum. 2.3 g of the expected product are obtained in the form of the fumarate; m.p.=244-245° C.

$\alpha_D^{20}$=+24.4° (c=0.25; MeOH).

Example 4

Compound 14

6-(3,4-Dichlorophenyl)-6-[2-[4-(3-fluorophenyl)-4-(2-oxo-1,3-oxazolidin-3-yl)piperid-1-yl]ethyl]-4-phenylmorpholin-3-one hydrochloride, dextrorotatory isomer (I)

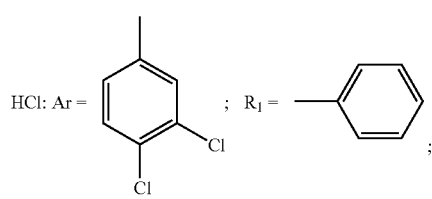

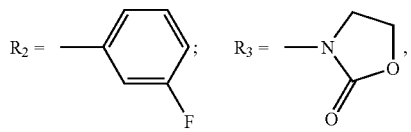

A mixture of 0.5 g of the compound obtained in Preparation 7.1, 0.36 g of the compound obtained in Preparation 8.13, 0.58 g of sodium triacetoxyborohydride and 0.0085 g of acetic acid in 50 ml of DCM is stirred overnight at rt. The reaction mixture is washed with 10% $Na_2CO_3$ solution, the organic phase is washed with water and dried over $Na_2SO_4$, and the solvent is evaporated off under vacuum. The residue is chromatographed on silica H gel, eluting with DCM and then with a DCM/MeOH mixture (99/1; v/v). The product obtained is dissolved in DCM, 2N hydrochloric ether is added, and the precipitate formed is filtered off by suction and washed with ether. 0.4 g of the expected product is obtained.

$\alpha_D^{20}$=+32.4° (c=0.5; MeOH).

$^1$H NMR: DMSO-$d_6$: δ (ppm): 2.3: mt: 2H, 2.4-3.7: m: 12H, 4.0-4.75: m: 6H, 7.0-7.9: m: 12H; 11: bs: 1H.

Example 5

Compound 15

6-(3,4-Dichlorophenyl)-6-[2-[4-(4-fluorophenyl)-4-2-oxo-1,3-oxazolidin-3-yl)piperid-1-yl]ethyl]-4-phenylmorpholin-3-one hydrochloride, dextrorotatory isomer

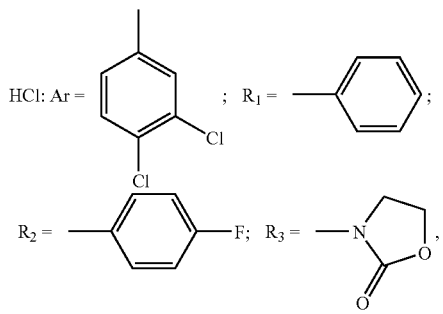

A mixture of 0.5 g of the compound obtained in Preparation 7.1, 0.36 g of the compound obtained in Preparation 8.14, 0.61 g of sodium triacetoxyborohydride and 0.0085 g of acetic acid in 50 ml of DCM is stirred overnight at rt. The reaction mixture is washed with 10% $Na_2CO_3$ solution, with water and dried over $Na_2SO_4$, and the solvent is evaporated off under vacuum. The residue is chromatographed on silica H gel, eluting with DCM and then with a DCM/MeOH mixture up to (100/3; v/v). The product obtained is dissolved in DCM, 2N hydrochloric ether is added, and the precipitate formed is filtered off by suction and washed with ether. 0.56 g of the expected product is obtained.

$\alpha_D^{20}=31°$ ($c=0.5$; MeOH).

$^1$H NMR: DMSO-$d_6$: δ (ppm): 2.3: mt: 2H, 2.4-3.7: m: 12H, 4.0-4.75: m: 6H, 7.0-7.9: m: 12H; 11: bs: 1H.

Table I below illustrates the chemical structures and the physical properties of a number of examples of compounds according to the invention. In this table:

in the "salt" column, "–" represents a compound in free base form, whereas "HCl" represents a compound in hydrochloride form and "$C_4H_4O_4$" represents a compound in fumarate form:

TABLE I

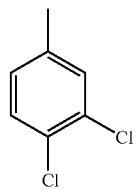

(I)

| Compound No. | Ar | $R_1$ | $R_2$ | $R_3$ | Salt | NMR $\alpha_D^{20}$ = (c; MeOH) MH$^+$, tr |
|---|---|---|---|---|---|---|
| 1 | 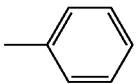 | 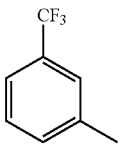 | 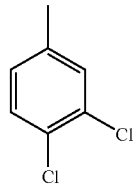 (CF$_3$) | —OH | HCl | +30° (c = 0.2) |
| 2 | 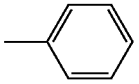 | 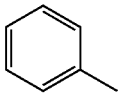 | 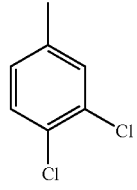 | —NHCOCH$_3$ | HCl | +31.8° (c = 0.5) |
| 3 | 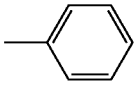 | (same as above) | 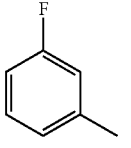 (F) | —NHCOCH$_3$ | HCl | +29.8° (c = 0.5) |

TABLE I-continued
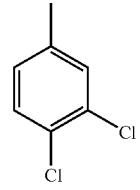
(I)
| Compound No. | Ar | R₁ | R₂ | R₃ | Salt | NMR $\alpha_D^{20}$ = (c; MeOH) MH⁺, tr |
|---|---|---|---|---|---|---|
| 4 | 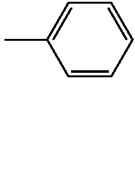 | 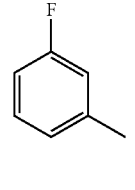 | 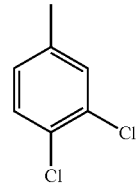 | —NHCOCH₃ | C₄H₄O₄ | +24.4° (c = 0.2) |
| 5 | 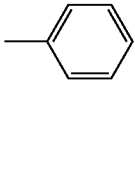 | 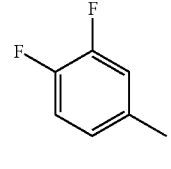 | 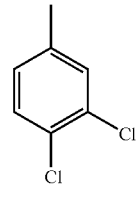 | —NHCOCH₃ | HCl | +30.4° (c = 0.5) |
| 6 | 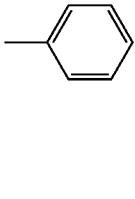 | 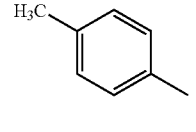 | 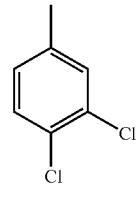 | —NHCOCH₃ | HCl | NMR MH⁺ = 580, tr = 6.75 |
| 7 | 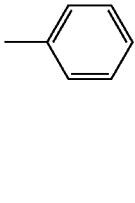 | 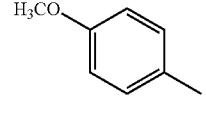 | 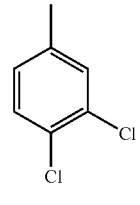 | —NHCOCH₃ | HCl | +11.9° (c = 0.5) |
| 8 | 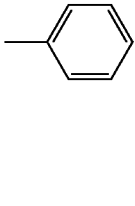 | 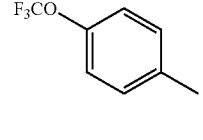 | 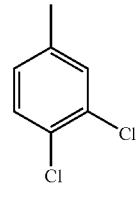 | —NHCOCH₃ | HCl | NMR MH⁺ = 650, tr = 7.17 |
| 9 | 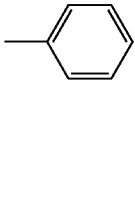 | 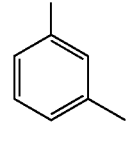 | 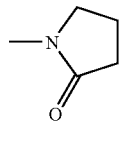 |  | HCl | +31.4° (c = 0.5) |

TABLE I-continued
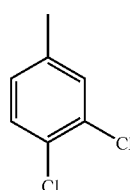
(I)
| Compound No. | Ar | R₁ | R₂ | R₃ | Salt | NMR $\alpha_D^{20}$ = (c; MeOH) MH⁺, tr |
|---|---|---|---|---|---|---|
| 10 | 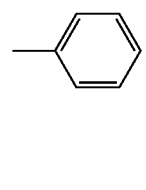 | 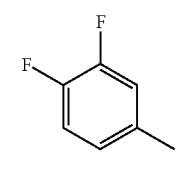 | 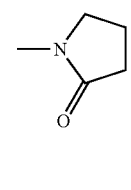 | 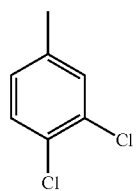 | HCl | +26.8° (c = 0.5) |
| 11 | 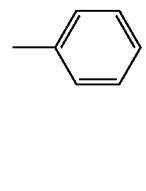 | 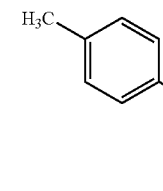 | 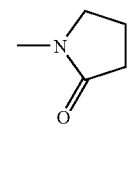 | 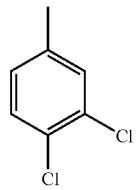 | HCl | NMR MH⁺ = 606, tr = 7.1 |
| 12 | 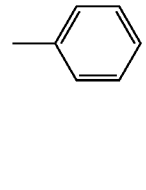 | 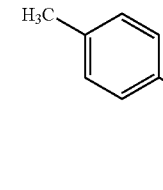 | 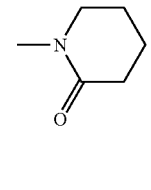 | 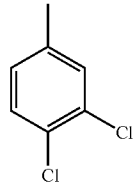 | HCl | +33.2° (c = 0.5) |
| 13 | 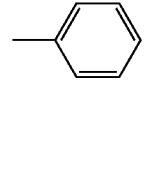 | 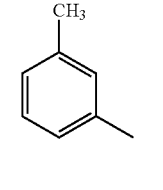 | 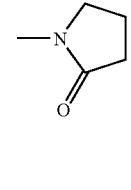 | 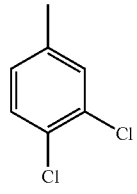 | HCl | +35.2° (c = 1) |
| 14 | 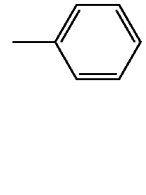 | 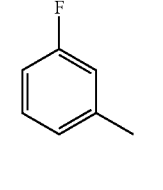 | 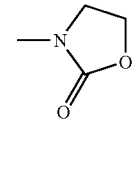 | 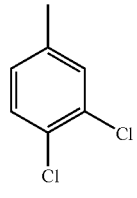 | HCl | +32.4° (c = 0.5) |
| 15 | 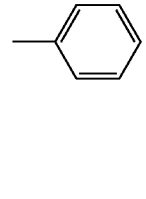 | 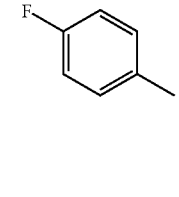 | 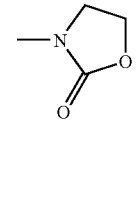 | | HCl | +31° (c = 0.5) |

TABLE I-continued

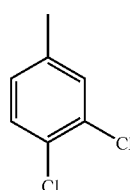
(I)

| Compound No. | Ar | R₁ | R₂ | R₃ | Salt | NMR<br>$\alpha_D^{20}$ = (c; MeOH)<br>MH⁺, tr |
|---|---|---|---|---|---|---|
| 16 | 3,4-diClC₆H₃ | phenyl | 2,4-diMeC₆H₃ | 2-oxo-oxazolidin-3-yl | HCl | +28° (c = 0.5) |
| 17 | 3,4-diClC₆H₃ | phenyl | phenyl | 2-oxo-1,3-oxazinan-3-yl | HCl | +33.2° (c = 0.5) |
| 18 | 3,4-diClC₆H₃ | phenyl | 4-FC₆H₄ | 2-oxo-1,3-oxazinan-3-yl | HCl | +37° (c = 0.5) |
| 19 | 3,4-diClC₆H₃ | phenyl | 3,4-diFC₆H₃ | 2-oxo-1,3-oxazinan-3-yl | HCl | NMR<br>MH⁺ = 644,<br>tr = 6.46 |
| 20 | 3,4-diClC₆H₃ | phenyl | phenyl | —CO—morpholin-4-yl | HCl | +29.2° (c = 0.2) |
| 21 | 3,4-diClC₆H₃ | phenyl | piperidin-1-yl | —CONH₂ | 2HCl | +32.4° (c = 0.2) |

TABLE I-continued (I)

R2, R3-substituted piperidine-N-CH2-CH2-C(Ar)(morpholin-3-one-N-R1)

| Compound No. | Ar | R1 | R2 | R3 | Salt | NMR $\alpha_D^{20}$ = (c; MeOH) MH+, tr |
|---|---|---|---|---|---|---|
| 22 | 3,4-dichlorophenyl | phenyl | 3,4-difluorophenyl | 3-(2-oxo-oxazolidin-3-yl) | HCl | +29.6° (c = 1) |
| 23 | 3,4-difluorophenyl | phenyl | phenyl | —NHCOCH3 | HCl | +23.4° (c = 0.5) |
| 24 | 3,4-difluorophenyl | phenyl | 4-(trifluoromethyl)phenyl | —NHCOCH3 | HCl | +17° (c = 0.5) |
| 25 | 3,4-difluorophenyl | phenyl | piperidin-1-yl | —CONH2 | 2HCl | +18.2° (c = 0.5) |
| 26 | 3,4-dichlorophenyl | phenyl | 3-(trifluoromethyl)phenyl | —NHCOCH3 | HCl | +29.2° (c = 0.1) |
| 27 | 3,4-dichlorophenyl | phenyl | pyridin-2-yl | —OH | HCl | +30.4° (c = 1) |

TABLE I-continued
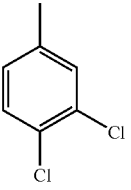
(I)
| Compound No. | Ar | $R_1$ | $R_2$ | $R_3$ | Salt | NMR<br>$\alpha_D^{20}$ = (c; MeOH)<br>$MH^+$, tr |
|---|---|---|---|---|---|---|
| 28 | 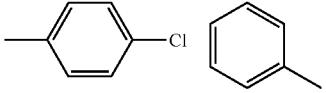 |  | 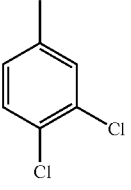 | —NHCOCH$_3$ | HCl | $MH^+$ = 600, tr = 7.02 |
| 29 | 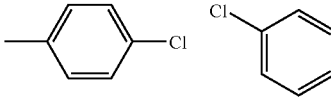 |  | 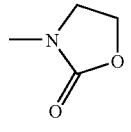 | 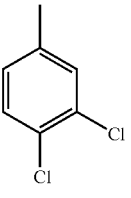 | HCl | $MH^+$ = 662, tr = 7.54 |
| 30 | 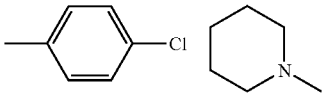 |  | 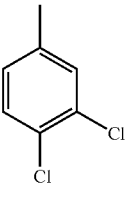 | —CON(CH$_3$)$_2$ | 2HCl | $MH^+$ = 621, tr = 7.45 |
| 31 | 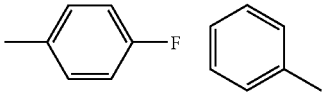 |  | 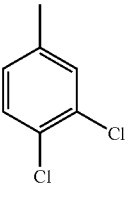 | —NHCOCH$_3$ | HCl | $MH^+$ = 584, tr = 6.69 |
| 32 | 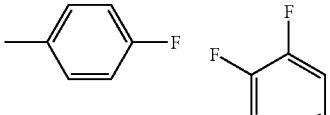 |  | 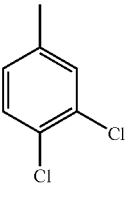 | —NHCOCH$_3$ | HCl | $MH^+$ = 620, tr = 6.93 |
| 33 | 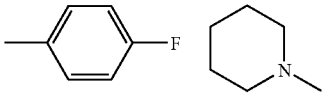 |  | | —CON(CH$_3$)$_2$ | 2HCl | $MH^+$ = 605, tr = 7.27 |

TABLE I-continued

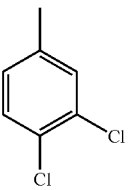

| Compound No. | Ar | $R_1$ | $R_2$ | $R_3$ | Salt | NMR<br>$\alpha_D^{20}$ = (c; MeOH)<br>$MH^+$, tr |
|---|---|---|---|---|---|---|
| 34 | 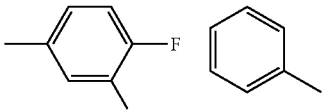 | 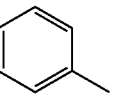 |  | —NHCOCH$_3$ | HCl | $MH^+$ = 602,<br>tr = 6.90 |

$^1$H NMR of compound 6: DMSO-d$_6$: δ (ppm): 1.87: s: 3H; 1.9-2.1: t: 2H; 2.25: s: 3H; 2.3-3.2: m: 8H; 3.3-3.5: t: 2H; 4.13: s: 2H; 4.42: dd: 2H; 7.0-7.6: m: 10H; 7.6-7.8: m: 2H; 8.0: bs: 1H; 10.2: bs: 1H.

$^1$H NMR of compound 8: DMSO-d$_6$: δ (ppm): 1.9: s: 3H, 2.1-2.4: m: 2H, 2.5-3.2: m: 8H, 3.3-3.6: m: 2H, 4.1: s: 2H, 4.4: dd: 2H, 7.2-7.6: m: 10H, 7.7-7.8: 2d: 2H, 8.2: s: 1H, 10.6: bs: 1H.

$^1$H NMR of compound 11: DMSO-d$_6$: δ (ppm): 1.7-2.2: m: 4H, 2.2-2.4: t+d: 5H, 2.4-3.2: m: 10H, 3.4-3.6: t: 2H, 4.14: s: 2H, 4.42: dd: 2H, 7.1-7.6: m: 10H, 7.6-7.8: m: 2H, 10.2: bs: 1H.

$^1$H NMR of compound 19: DMSO-d$_6$: δ (ppm): 1.8-1.9: m: 2H, 2.19: t: 2H, 2.3-3.2: m: 9H, 3.2-3.6: m: 3H, 3.9-4.2: m: 4H, 4.4: dd: 2H, 7.1-7.6: m: 9H, 7.6-7.8: m: 2H, 10.5: bs: 1H.

The compounds according to the invention underwent pharmacological trials.

The affinity of the compounds for the tachykinin receptors NK$_2$ was evaluated in vitro by measuring the inhibition of the binding of [$^{125}$I]His-neurokinin A ([$^{125}$I]His-NKA) to cloned human NK$_2$ receptors expressed by CHO cells (Y. Takeda et al., J. Neurochem., 1992, 59, 740-745).

The trials were performed according to

Emonds-Alt et al. (J. Pharmacol. Exp. Ther., 2002, 303, 1171-1179).

The compounds according to the invention strongly inhibit the binding of [$^{125}$I]His-NKA to the cloned human NK$_2$ receptors expressed in CHO cells, with an inhibition constant Ki of between 50 nM and 0.05 nM. Thus, compound 3 has an inhibition constant (Ki) equal to 0.16 nM.

The compounds of the present invention were also evaluated in vivo in a model of pharmacodynamics.

In mice, injection into the striatum of a specific agonist of the NK$_2$ receptor, [Nle$^{10}$]NKA(4-10), causes a spinning behavior, which is inhibited in a dose-dependent manner by the compounds according to the invention administered orally. This test was performed according to Poncelet et al. (Neurosci. Lett., 1993, 149, 40-42). In this test, compound 3 has a 50 effective dose (ED$_{50}$) of 0.023 mg per kg orally.

These pharmacological results show that the compounds according to the invention, in particular compound 3, are antagonists of the NK$_2$ receptors by blocking the pharmacological effects caused by neurokinin A. Furthermore, these results show that the compounds according to the invention do indeed cross the blood-brain barrier and are orally active.

According to another of its aspects, the present invention relates to the use of the compounds of formula (I) or a pharmaceutically acceptable salt, solvate and/or hydrate thereof, for the preparation of medicinal products for treating and preventing any central and/or peripheral pathology in which neurokinin A, via its NK$_2$ receptor, is involved.

The compounds according to the invention may thus be used for the preparation of medicinal products, in particular medicinal products that are antagonists of the NK$_2$ receptors of neurokinin A.

Thus, according to another of its aspects, a subject of the invention is medicinal products that comprise a compound of formula (I), or a pharmaceutically acceptable acid-addition salt thereof, or alternatively a hydrate or a solvate of the compound of formula (I).

These medicinal products find their therapeutic use and are especially useful:

as analgesics, in particular in the treatment of traumatic pain such as post-operative pain; neuralgia of the brachial plexus; chronic pain such as arthritic pain caused by osteoarthritis, rheumatoid arthritis or psoriatic arthritis; neuropathic pain such as post-herpetic neuralgia, trigeminal neuralgia, segmental or intercostal neuralgia, fibromyalgia, causalgia, peripheral neuropathy, diabetic neuropathy, neuropathies induced by a chemotherapy, AIDS-related neuropathies, occipital neuralgia, geniculate neuralgia or glossopharyngeal neuralgia; the illusory pain of amputees; various forms of headache such as chronic or acute migraine, temporomandibular pain, maxillary sinus pain, facial neuralgism or odontalgia; pain experienced by cancer sufferers; pain of visceral origin; gastrointestinal pain; pain caused by compression of a nerve, pain caused by intensive sporting activity; dysmenorrhoea; menstrual pain; pain caused by meningitis or arachnoiditis; musculoskeletal pain; pain in the lower back caused by a spinal stenosis, a prolapsed disc or sciatica; pain experienced by angina sufferers; pain caused by an ankylosing spondylitis; pain associated with gout; pain associated with burns, cicatrization or pruriginous dermatosis; thalamic pain;

as anti-inflammatory agents, in particular for treating inflammations in asthma, influenza, chronic bronchitis (in particular obstructive chronic bronchitis and COPD (chronic obstructive pulmonary disease)), coughing, allergies, bronchospasm and rheumatoid arthritis;

inflammatory diseases of the gastrointestinal system, for example Crohn's disease, ulcerative colitis, pancreatitis, gastritis, intestinal inflammation, disorders caused by non-steroidal anti-inflammatory agents, inflammatory and secretory effects caused by bacterial infections, for example caused by *Clostridium difficile*; inflammatory skin diseases, for example herpes and eczema; inflammatory bladder diseases such as cystitis and urinary incontinence; ophthalmic inflammations such as conjunctivitis and vitreoretinopathy; dental inflammations such as gingivitis and periodontitis;

in the treatment of allergic diseases, in particular of the skin, such as urticaria, contact dermatitis, atopic dermatitis and respiratory diseases such as rhinitis;

in the treatment of diseases of the central nervous system, in particular psychoses such as schizophrenia, mania and dementia; cognitive disorders such as Alzheimer's disease, anxiety, AIDS-related dementia, diabetic neuropathies; depression; Parkinson's disease; drug dependency; substance abuse; consciousness disorders, sleeping disorders, disorders of the circadian rhythm, mood disorders and epilepsy; Down's syndrome; Huntington's chorea; stress-related somatic disorders; neurodegenerative diseases such as Pick's disease or Creutzfeldt-Jacob disease; disorders associated with panic, phobia or stress; compulsive obsessive disorders; tics; bipolar disorders; schizoaffective disorders; personality disorders; disorders associated with attention deficit or hyperactivity;

in the treatment of modifications of the permeability of the blood-brain barrier during inflammatory and autoimmune processes of the central nervous system, for example during AIDS-related infections;

as muscle relaxants and antispasmodic agents;

in the treatment of acute or delayed and anticipated nausea and vomiting, for example nausea and vomiting induced by drugs such as the agents used in chemotherapy in the case of cancer; by radiation therapy during irradiation of the thorax or the abdomen in the treatment of cancer or carcinoidosis; by ingestion of poison; by toxins caused by metabolic or infectious disorders such as gastritis, or produced during a bacterial or viral gastrointestinal infection; during pregnancy; during vestibular disorders such as travel sickness, vertigo or Ménière's disease; in post-operative diseases; the nausea and vomiting induced by dialysis or by prostaglandins; by gastrointestinal obstructions; in reduced gastrointestinal motility; in visceral pain caused by myocardial infarction or peritonitis; in migraine; in altitude sickness; by ingestion of opiate analgesics such as morphine; in gastro-oesophageal reflux; in acidic indigestion or over-consumption of food or drink, in gastric acidity or acor, regurgitation, and heartburn, for example episodic or nocturnal heartburn or heartburn induced by a meal and dyspepsia;

in the treatment of diseases of the gastrointestinal system such as irritable bowel syndrome, gastric and duodenal ulcers, oesophageal ulcers, diarrhea, hypersecretions, lymphomas, gastrites, gastro-oesophageal reflux, fecal incontinence and Hirschsprung's disease;

in the treatment of skin diseases such as psoriasis, pruritus and burns, in particular sunburn;

in the treatment of diseases of the cardiovascular system such as hypertension, the vascular aspects of migraine, oedema, thrombosis, angina pectoris, vascular spasms, circulatory diseases caused by vasodilation, Raynaud's disease, fibrosis, collagen diseases, atherosclerosis and preeclampsia;

in the treatment of small-cell and large-cell lung cancer; breast cancer; cerebral tumors and adenocarcinomas of the urogenital sphere; in adjuvant treatment for preventing metastases;

demyelination diseases such as multiple sclerosis or amyotrophic lateral sclerosis;

in the treatment of diseases of the immune system associated with suppression or stimulation of the functions of the immune cells, for example rheumatoid arthritis, psoriasis, Crohn's disease, diabetes, lupus and rejection reactions after transplantation;

in the treatment of miction disorders, in particular pollakiuria, exertion incontinence, urgency incontinence and post-partum incontinence;

in the treatment of prostate hypertrophy;

in the treatment of histiocytic reticulosis, for instance in lymphatic tissues;

as anorexigenic agents;

in the treatment of emphysema; Reiter's disease; haemorrhoids;

in the treatment of ocular diseases such as glaucoma, ocular hypertension, myosis and excessive lachrymal secretion;

in the treatment or prevention of an epileptic fit, cranial trauma, spinal cord trauma, cerebral ischaemic lesions caused by vascular attack or occlusion;

in the treatment of disorders of heart rate and cardiac rhythm, in particular those occasioned by pain or stress;

in the treatment of sensitive skin and for preventing or combating irritation of the skin or mucous membranes, dandruff, erythema or pruritus;

in the treatment of neurological skin disorders such as lichens, prurigo, pruriginous toxidermia and severe pruritus of neurogenic origin;

in the treatment of ulcers and of all diseases caused by *Helicobacter pylori* or a urease-positive gram-negative bacterium;

in the treatment of diseases caused by angiogenesis or in which angiogenesis is a symptom;

in the treatment of ocular and/or palpebral algia and/or ocular or palpebral dysesthesia;

as antiperspirants.

According to the present invention, the compounds of formula (I) are most particularly useful for the treatment of irritable bowel syndrom (IBS); fibromyalgia; neuropathic pain; chronic fatigue syndrome; migraine; atypic facial pain; Crohn's disease; ulcerative colitis; constipation; diarrhoea; gastro-oesophageal reflux; gastritis; pancreatitis; major depression; anxiety such as generalized anxiety, social, phobic and panic anxiety; compulsive obsessive disorders; tics; mania; bipolar disorders; schizophrenia; schizoaffective disorders; personality disorders; psychotic disorders; disorders associated with attention deficit or hyperactivity; disorders caused by the use of addictive substances; prostate hypertrophy.

According to another of its aspects, the present invention relates to pharmaceutical compositions comprising, as active principle, a compound according to the invention. These pharmaceutical compositions contain an effective dose of at least one compound according to the invention, or a pharmaceutically acceptable salt thereof, a solvate or hydrate of the said compound, and also at least one pharmaceutically acceptable excipient.

The said excipients are chosen, according to the pharmaceutical form and the desired mode of administration, from the usual excipients known to those skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or the possible salt, solvate or hydrate thereof, may be administered in unit administration form, as a mixture with standard pharmaceutical excipients, to animals and to human beings for the prophylaxis or treatment of the above disorders or diseases.

The appropriate unit administration forms include oral forms such as tablets, soft or hard gel capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms and implants. For topical application, the compounds according to the invention may be used in creams, gels, ointments or lotions.

By way of example, a unit administration form of a compound according to the invention in the form of a tablet may comprise the following components:

| Compound according to the invention | 50.0 mg |
|---|---|
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

Via the oral route, the dose of active principle administered per day may reach 0.01 to 100 mg/kg, in one or more dosage intakes, preferably 0.02 to 50 mg/kg.

There may be particular cases in which higher or lower doses are appropriate; such doses do not depart from the scope of the invention. According to the usual practice, the dosage that is appropriate for each patient is determined by the doctor according to the mode of administration and the weight and response of the said patient.

According to another of its aspects, the present invention also relates to a method for treatment of the pathologies mentioned above, which comprises the administration to a patient of an effective dose of a compound according to the invention, or a pharmaceutically acceptable salt thereof or hydrates or solvates thereof.

What is claimed is:

1. A compound corresponding to formula (I):

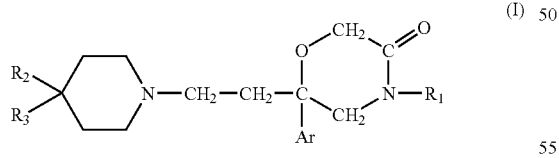

(I)

in which:
Ar represents a phenyl mono- or di-substituted with a halogen atom;
$R_1$ represents a phenyl that is un-substituted or substituted once or twice with one or two substituents independently chosen from a halogen atom, a $(C_1-C_4)$alkyl and a $(C_1-C_4)$alkoxy;
$R_2$ represents:
  a pyridyl;
  a phenyl that is un-substituted or substituted once or twice with one or two substituents independently chosen from a halogen atom, a $(C_1-C_4)$alkyl, a $(C_1-C_4)$alkoxy, a trifluoromethyl group and a trifluoromethoxy group;
  a benzyl that is un-substituted or substituted on the phenyl once or twice with one or two substituents independently chosen from a halogen atom, a $(C_1-C_4)$alkyl, a $(C_1-C_4)$alkoxy, a trifluoromethyl group and a trifluoromethoxy group;
$R_2$ may also represent:
  a heterocyclic radical chosen from azetidine, pyrrolidine, piperidine, morpholine, thiomorpholine or perhydroazepine when $R_3$ represents a cyano or a group —$CONR_{11}R_{12}$;
$R_3$ represents a group chosen from:
(1) a hydrogen atom;
(2) $(C_1-C_4)$ alkyl;
(3) $(C_1-C_4)$ alkylcarbonyl;
(4) cyano;
(5) —$(CH_2)_q$—OH;
(6) —$(CH_2)_q$—O—$(C_1-C_4)$alkyl;
(7) —$(CH_2)_q$—O—CO—$R_4$;
(8) —$(CH_2)_q$—O—CO—NH—$(C_1-C_4)$alkyl;
(9) —$NR_5R_6$;
(10) —$(CH_2)_q$—$NR_7COR_8$;
(11) —$(CH_2)_q$—$NR_7COOR_9$;
(12) —$(CH_2)_q$—$NR_7SO_2R_{10}$;
(13) —$(CH_2)_q$—$NR_7CONR_{11}R_{12}$;
(14) —$CH_2NR_{13}R_{14}$;
(15) —$CH_2$—$CH_2NR_{13}R_{14}$;
(16) —COOH;
(17) —COO—$(C_1-C_4)$ alkyl;
(18) —$CONR_{11}R_{12}$;
(19) —$CH_2$—COOH;
(20) —$CH_2$—COO—$(C_1-C_4)$alkyl;
(21) —$CH_2$—$CONR_{11}R_{12}$;
(22) —O—$CH_2CH_2OR_{15}$;
(23) —$NR_7COCOR_{16}$;
(24) —$CONR_7$—$NR_{17}R_{18}$;

(25)

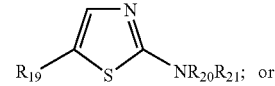

; or (26)

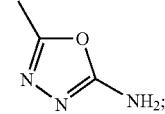

q is 0, 1 or 2;
$R_4$ represents a $(C_1-C_4)$alkyl; a $(C_3-C_7)$cycloalkyl that is un-substituted or substituted with one or more methyl groups; a phenyl, or a pyridyl;
$R_5$ and $R_6$ each independently represent a hydrogen atom or a $(C_1-C_4)$alkyl; $R_6$ may also represent a $(C_3-C_7)$cycloalkylmethyl, a benzyl or a phenyl; or $R_5$ and $R_6$, together with the nitrogen atom to which they are attached, constitute a heterocycle chosen from azetidine, pyrrolidine, piperidine, morpholine thiomorpholine, perhydroazepine or piperazine that is un-substituted or substituted in position 4 with a $(C_1-C_4)$alkyl;
$R_7$ represents a hydrogen atom or a $(C_1-C_4)$alkyl;
$R_8$ represents a hydrogen atom; a $(C_1-C_4)$alkyl; a vinyl; a phenyl; a benzyl; a pyridyl; or a $(C_3-C_7)$cycloalkyl that is un-substituted or substituted with one or more methyl groups; a furyl; a thienyl; a pyrrolyl; an imidazolyl;

or $R_7$ and $R_8$ together represent a group $—(CH_2)_p—$;

p is 3 or 4;

$R_9$ represents a $(C_1-C_4)$ alkyl or a phenyl;

or $R_7$ and $R_9$ together represent a group $—(CH_2)_n—$;

n is 2 or 3;

$R_{10}$ represents a $(C_1-C_4)$ alkyl or an amino that is free or substituted with one or two $(C_1-C_4)$alkyls; a phenyl that is un-substituted or substituted one or more times with a substituent chosen from: a halogen atom, a $(C_1-C_4)$ alkyl, a trifluoromethyl, a hydroxyl, a $(C_1-C_4)$alkoxy, a carboxyl, a $(C_1-C_4)$alkoxycarbonyl, a $(C_1-C_4)$alkylcarbonyloxy, a cyano, a nitro, an amino that is free or substituted with one or two $(C_1-C_4)$alkyls, the said substituents being identical or different;

$R_{11}$ and $R_{12}$ each independently represent a hydrogen or a $(C_1-C_4)$ alkyl; $R_{12}$ may also represent a $(C_3-C_7)$cycloalkyl, a $(C_3-C_7)$cycloalkylmethyl, a hydroxyl, a $(C_1-C_4)$alkoxy, a benzyl or a phenyl; or $R_{11}$ and $R_{12}$, together with the nitrogen atom to which they are attached, constitute a heterocycle chosen from azetidine, pyrrolidine, piperidine, morpholine thiomorpholine and perhydroazepine;

or $R_7$ and $R_{12}$ together represent a group $—(CH_2)_m—$;

m is 2 or 3;

$R_{13}$ and $R_{14}$ each independently represent a hydrogen atom or a $(C_1-C_4)$alkyl; $R_{14}$ may also represent a $(C_3-C_7)$ cycloalkylmethyl or a benzyl;

$R_{15}$ represents a hydrogen atom; a $(C_1-C_4)$alkyl; a formyl; a $(C_1-C_4)$alkylcarbonyl;

$R_{16}$ represents a $(C_1-C_4)$alkoxy;

$R_{17}$ and $R_{18}$ each independently represent a hydrogen atom or a $(C_1-C_4)$alkyl;

or alternatively $R_{17}$ and $R_{18}$, together with the nitrogen atom to which they are attached, constitute a heterocycle chosen from pyrrolidine, piperidine and morpholine;

$R_{19}$ represents a hydrogen atom or a $(C_1-C_4)$alkyl;

$R_{20}$ and $R_{21}$ each independently represent a hydrogen atom or a $(C_1-C_4)$ alkyl; $R_{21}$ may also represent a formyl or a $(C_1-C_4)$alkylcarbonyl;

in the form of its' acid-addition salt or hydrate or a solvate of said compound.

2. The compound of formula (I) as recited in to claim 1, wherein:

Ar represents a phenyl di-substituted with a halogen atom;

$R_1$ represents a phenyl that is un-substituted or substituted once or twice with a halogen atom;

$R_2$ represents:

a pyridyl;

a phenyl that is un-substituted or substituted once or twice with one or two substituents independently chosen from a halogen atom, a $(C_1-C_4)$alkyl, a $(C_1-C_4)$ alkoxy, a trifluoromethyl group and a trifluoromethoxy group;

$R_2$ may also represent a heterocyclic radical chosen from azetidine, pyrrolidine, piperidine, morpholine, thiomorpholine and perhydroazetidine when $R_3$ represents a group $—CONR_{11}R_{12}$;

$R_3$ represents a group chosen from:

(5) $—(CH_2)_q—OH$ in which q is 0;

(10) $—(CH_2)_q—NR_7COR_8$ in which q is 0;

(11) $—(CH_2)_q—NR_7COOR_9$ in which q is 0;

(18) $—CONR_{11}R_{12}$;

$R_7, R_8, R_9, R_{11}$ and $R_{12}$ being as defined for a compound of formula (I) in claim 1; also in in the form of its' acid-addition salt, or a hydrate or a solvate of said compound.

3. The compound of formula (I) as recited in claim 1, wherein:

Ar represents a 3,4-dichlorophenyl or a 3,4-difluorophenyl;

$R_1$ represents a phenyl, a 4-chlorophenyl, a 4-fluorophenyl or a 3,4-difluorophenyl;

$R_2$ represents:

a 2-pyridyl;

a phenyl, a 4-chlorophenyl, a 3-fluorophenyl, a 4-fluorophenyl, a 3,4-difluorophenyl, a 3-methylphenyl, a 3,4-dimethylphenyl, a 4-methoxyphenyl, a 3-(trifluoromethyl)phenyl, a 4-(trifluoromethyl)phenyl or a 4-(trifluoromethoxy)phenyl;

$R_2$ may also represent a 1-piperidyl when $R_3$ represents a $—CONH_2$ group or a $—CON(CH_3)_2$ group;

$R_3$ represents a group chosen from:

a hydroxyl;

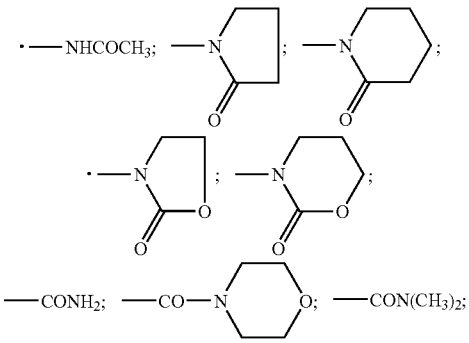

DPP-IV exists as both a membrane-spanning form present in cells throughout the body and a soluble circulating form. Both forms of DPP-IV have identical enzymatic activity (9) and cleave a wide range of bioactive peptides in vitro, including hormones, neuropeptides, and chemokines (12). One potential regulatory role of DPP-IV is the inactivation of GHRH through cleavage of the active form, GHRH(1-44)-$NH_2$, to the N-terminally shortened inactive form, GHRH(3-44)-$NH_2$, in the form of its' acid-addition salts, or a hydrate or a solvate of said compound.

4. The compound as recited in claim 1, selected from the group consisting of:

-6-(3,4-dichlorophenyl)-6-[2-[4-hydroxy-4-[3-(trifluoromethyl)phenyl]-1-piperidyl]ethyl]-4-phenylmorpholin-3-one, dextrorotatory isomer;

—N-[1-[2-[2-(3,4-dichlorophenyl)-5-oxo-4-phenylmorpholin-2-yl]ethyl]-4-phenyl-4-piperidyl]-acetamide, dextrorotatory isomer;

—N-[1-[2-[2-(3,4-dichlorophenyl)-5-oxo-4-phenylmorpholin-2-yl]ethyl]-4-(3-fluorophenyl)-4-piperidyl]acetamide, dextrorotatory isomer;

—N-[1-[2-[2-(3,4-dichlorophenyl)-5-oxo-4-phenylmorpholin-2-yl]ethyl]-4-(3,4-difluorophenyl)-4-piperidyl]acetamide, dextrorotatory isomer;

—N-[1-[2-[2-(3,4-dichlorophenyl)-5-oxo-4-phenylmorpholin-2-yl]ethyl]-4-(4-methylphenyl)-4-piperidyl]acetamide, dextrorotatory isomer;

—N-[1-[2-[2-(3,4-dichlorophenyl)-5-oxo-4-phenylmorpholin-2-yl]ethyl]-4-(4-methoxyphenyl)-4-piperidyl]acetamide, dextrorotatory isomer;
—N-[1-[2-[2-(3,4-dichlorophenyl)-5-oxo-4-phenylmorpholin-2-yl]ethyl]-4-[4-(trifluoromethoxy)-phenyl]-4-piperidyl]acetamide, dextrorotatory isomer;
-6-(3,4-dichlorophenyl)-6-[2-[4-(3-fluoro-phenyl)-4-(2-oxopyrrolidin-1-yl)-1-piperidyl]ethyl]-4-phenylmorpholin-3-one, dextrorotatory isomer;
-6-(3,4-dichlorophenyl)-6-[2-[4-(3,4-di-fluorophenyl)-4-(2-oxopyrrolidin-1-yl)-1-piperidyl]-ethyl]-4-phenyl-morpholin-3-one, dextrorotatory isomer;
-6-(3,4-dichlorophenyl)-6-[2-[4-(4-methyl-phenyl)-4-(2-oxopyrrolidin-1-yl)-1-piperidyl]ethyl]-4-phenylmorpholin-3-one, dextrorotatory isomer;
-1'-[2-[2-(3,4-dichlorophenyl)-5-oxo-4-phenylmorpholin-2-yl]ethyl]-4'-(4-methylphenyl)-1,4'-bipiperidin-2-one, dextrorotatory isomer;
-6-(3,4-dichlorophenyl)-6-[2-[4-(3-methyl-phenyl)-4-(2-oxopyrrolidin-1-yl)-1-piperidyl]ethyl]-4-phenylmorpholin-3-one, dextrorotatory isomer;
-6-(3,4-dichlorophenyl)-6-[2-[4-(3-fluoro-phenyl)-4-(2-oxo-1,3-oxazolidin-3-yl)-1-piperidyl]-ethyl]-4-phenylmorpholin-3-one, dextrorotatory isomer;
-6-(3,4-dichlorophenyl)-6-[2-[4-(4-fluoro-phenyl)-4-(2-oxo-1,3-oxazolidin-3-yl)-1-piperidyl]-ethyl]-4-phenylmorpholin-3-one, dextrorotatory isomer;
-6-(3,4-dichlorophenyl)-6-[2-[4-(3,4-dimethyl-phenyl)-4-(2-oxo-1,3-oxazolidin-3-yl)-1-piperidyl]-ethyl]-4-phenylmorpholin-3-one, dextrorotatory isomer;
-3-[1-[2-[2-(3,4-dichlorophenyl)-5-oxo-4-phenylmorpholin-2-yl]ethyl]-4-phenyl-4-piperidyl]-1,3-oxazinan-2-one, dextrorotatory isomer;
-3-[1-[2-[2-(3,4-dichlorophenyl)-5-oxo-4-phenylmorpholin-2-yl]ethyl]-4-(4-fluorophenyl)-4-piperidyl]-1,3-oxazinan-2-one, dextrorotatory isomer;
-3-[1-[2-[2-(3,4-dichlorophenyl)-5-oxo-4-phenylmorpholin-2-yl]ethyl]-4-(3,4-difluorophenyl)-4-piperidyl]-1,3-oxazinan-2-one, dextrorotatory isomer;
-6-(3,4-dichlorophenyl)-6-[2-[4-(morpholin-4-ylcarbonyl)-4-phenyl-1-piperidyl]ethyl]-4-phenylmorpholin-3-one, dextrorotatory isomer;
-1'-[2-[2-(3,4-dichlorophenyl)-5-oxo-4-phenylmorpholin-2-yl]ethyl]-1,4'-bipiperidin-4'-carboxamide, dextrorotatory isomer;
-6-(3,4-dichlorophenyl)-6-[2-[4-(3,4-di-fluorophenyl)-4-(2-oxo-1,3-oxazolidin-3-yl)-1-piperidyl]ethyl]-4-phenylmorpholin-3-one, dextrorotatory isomer;
—N-[1-[2-[2-(3,4-difluorophenyl)-5-oxo-4-phenylmorpholin-2-yl]ethyl]-4-phenyl-4-piperidyl]-acetamide, dextrorotatory isomer;
—N-[1-[2-[2-(3,4-dichlorophenyl)-5-oxo-4-phenylmorpholin-2-yl]ethyl]-4-[4-(trifluoromethyl)-phenyl]-4-piperidyl]acetamide, dextrorotatory isomer;
-1'-[2-[2-(3,4-difluorophenyl)-5-oxo-4-phenylmorpholin-2-yl]ethyl]-1,4'-bipiperidine-4'-carboxamide, dextrorotatory isomer;
—N-[1-[2-[2-(3,4-dichlorophenyl)-5-oxo-4-phenylmorpholin-2-yl]ethyl]-4-[3-(trifluoromethyl)-phenyl]-4-piperidyl]acetamide, dextrorotatory isomer;
-6-(3,4-dichlorophenyl)-6-[2-(4-hydroxy-4-pyridin-2-yl-1-piperidyl)ethyl]-4-phenylmorpholin-3-one, dextrorotatory isomer;
—N-[1-[2-[4-(4-chlorophenyl)-2-(3,4-dichloro-phenyl)-5-oxomorpholin-2-yl]ethyl]-4-phenyl-4-piperidyl]acetamide;
-4-(4-chlorophenyl)-6-[2-[4-(4-chlorophenyl)-4-(2-oxo-1,3-oxazolidin-3-yl)-1-piperidyl]ethyl]-6-(3,4-dichlorophenyl)morpholin-3-one;
-1'-[2-[4-(4-chlorophenyl)-2-(3,4-dichloro-phenyl)-5-oxomorpholin-2-yl]ethyl]-N,N-dimethyl-1,4'-bipiperidine-4'-carboxamide;
—N-[1-[2-[2-(3,4-dichlorophenyl)-4-(4-fluoro-phenyl)-5-oxomorpholin-2-yl]ethyl]-4-phenyl-4-piperidyl]acetamide;
—N-[1-[2-[2-(3,4-dichlorophenyl)-4-(4-fluoro-phenyl)-5-oxomorpholin-2-yl]ethyl]-4-(3,4-difluoro-phenyl)-4-piperidyl]acetamide;
-1'-[2-[2-(3,4-dichlorophenyl)-4-(4-fluoro-phenyl)-5-oxomorpholin-2-yl]ethyl]-N,N-dimethyl-1,4'-bipiperidine-4'-carboxamide;
—N-[1-[2-[2-(3,4-dichlorophenyl)-4-(3,4-di-fluorophenyl)-5-oxomorpholin-2-yl]ethyl]-4-phenyl-4-piperidyl]acetamide;

in the form of its' acid-addition salt or hydrate or a solvate of said compound.

5. The compound as recited in claim 1 selected from the group comprising:
—N-[1-[2-[2-(3,4-dichlorophenyl)-5-oxo-4-phenylmorpholin-2-yl]ethyl]-4-(3-fluorophenyl)-piperid-4-yl]acetamide, dextrorotatory isomer; in the form of its' acid-addition salt or hydrate or a solvate of said compound.

6. A process for the preparation of a compound of formula (I) as recited in claim 1 wherein the compound of formula II:

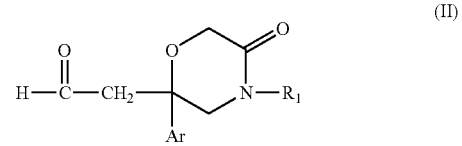

and Ar and $R_1$ are as defined in claim 1, is reacted with a compound of formula III in which $R_2$ and $R_3$ are as defined in claim 1:

in the presence of an acid in a solvent, and the intermediate aminium salt formed thereby is then reduced using a reducing agent.

7. A process for preparing a compound of formula (I) as recited in claim 1 wherein a compound of formula IV:

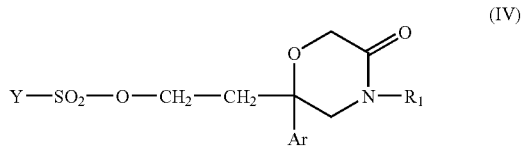

in which Ar and $R_1$ are as defined for a compound of formula (I) in claim 1, and Y represents a methyl, phenyl, tolyl or trifluoromethyl group, is reacted with a compound of formula:

(III)

in which $R_2$ and $R_3$ are as defined for a compound of formula (I) in claim 1.

8. A pharmaceutical composition comprising a compound of formula (I) according to claim 5, or a pharmaceutically acceptable salt, hydrate or a solvate thereof in combination with at least one pharmaceutically acceptable excipient.

* * * * *